(12) United States Patent
Yonemaru et al.

(10) Patent No.: US 11,349,128 B2
(45) Date of Patent: May 31, 2022

(54) ELECTRICALLY CONDUCTIVE SUBSTANCE, METHOD OF PRODUCING ELECTRICALLY CONDUCTIVE SUBSTANCE, AND ELECTRODE, CATALYST AND MATERIAL CONTAINING ELECTRICALLY CONDUCTIVE SUBSTANCE

(71) Applicant: ZEON CORPORATION, Tokyo (JP)

(72) Inventors: Hiroyuki Yonemaru, Tokyo (JP); Tsutomu Fujii, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 186 days.

(21) Appl. No.: 16/641,646

(22) PCT Filed: Aug. 13, 2018

(86) PCT No.: PCT/JP2018/030213
§ 371 (c)(1),
(2) Date: Feb. 25, 2020

(87) PCT Pub. No.: WO2019/044478
PCT Pub. Date: Mar. 7, 2019

(65) Prior Publication Data
US 2021/0075025 A1 Mar. 11, 2021

(30) Foreign Application Priority Data
Aug. 28, 2017 (JP) .............................. JP2017-163224

(51) Int. Cl.
*H01B 1/00* (2006.01)
*H01M 4/88* (2006.01)
(Continued)

(52) U.S. Cl.
CPC .............. *H01M 4/88* (2013.01); *C07C 327/38* (2013.01); *H01B 1/121* (2013.01); *H01B 1/122* (2013.01);
(Continued)

(58) Field of Classification Search
CPC ........... H01B 1/06; H01B 1/10; H01B 1/121; H01B 1/122; H01M 4/86; H01M 4/88
See application file for complete search history.

(56) References Cited

U.S. PATENT DOCUMENTS 5,041,654 A * 8/1991 Olson ..................... B41M 5/132
554/42
2012/0296095 A1 11/2012 Savonnet et al.
(Continued)

FOREIGN PATENT DOCUMENTS

CN 102936239 A 2/2013
JP S5857267 A 4/1983
(Continued)

OTHER PUBLICATIONS

Abboudi et al "Metal Complexes of Rubeanic Acid. 3.1 Large-Angle X-ray Scattering Studies of Amorphous Copper(II) and Nickel(II) COmplexes", Inorganic Chemistry, vol. 24, No. 13, 1985 pp. 2091-2094.*
(Continued)

*Primary Examiner* — Mark Kopec
(74) *Attorney, Agent, or Firm* — Kenja IP Law PC

(57) ABSTRACT

Disclosed is an electrically conductive substance which comprises a complex containing rubeanic acid ligands and copper ions. The copper ions contained in the complex comprise copper (I) ions. The electrically conductive substance is produced by a production method which comprises mixing a rubeanic acid compound and a copper (I) compound in the presence of a base.

14 Claims, 13 Drawing Sheets

(51) Int. Cl.
*H01M 4/86* (2006.01)
*H01B 1/12* (2006.01)
*C07C 327/38* (2006.01)
*H01M 4/90* (2006.01)

(52) U.S. Cl.
CPC ........ *H01M 4/8605* (2013.01); *H01M 4/9041* (2013.01)

(56) References Cited

U.S. PATENT DOCUMENTS

| 2013/0306488 A1 | 11/2013 | Taniguchi et al. |
| 2014/0212754 A1 | 7/2014 | Mokudai et al. |

FOREIGN PATENT DOCUMENTS

| JP | H0574458 A | 3/1993 |
| JP | 2004031174 A | 1/2004 |
| JP | 2007173173 A | 7/2007 |
| TW | 201134829 A1 | 10/2011 |
| WO | 2013035829 A1 | 3/2013 |
| WO | 2015171791 A1 | 11/2015 |

OTHER PUBLICATIONS

English language machine translation of JP 05074458 A (pub Mar. 1993).*
English language machine translation of JP 2007-173173 A (pub Jul. 2007).*
English language machine translation of JP 2004-031174 A (pub Jan. 2004).*
Apr. 20, 2021, the Extended European Search Report issued by the European Patent Office in the corresponding European Patent Application No. 18851962.3.
B. Slootmaekers et al., Thermal analysis of some Au(III) and Cu(I) dithiooxamide complexes, Thermochimica Acta, 1998, pp. 141-147, vol. 311.
Hiroshi Kitagawa et al., Highly proton-conductive copper coordination polymer, H2dtoaCu (H2dtoa=dithiooxamide anion), Inorganic Chemistry Communications, 2003, pp. 346-348, vol. 6.
Oct. 2, 2018, International Search Report issued in the International Patent Application No. PCT/JP2018/030213.
Mar. 3, 2020, International Preliminary Reporton Patentability issued in the International Patent Application No. PCT/JP2018/030213.

* cited by examiner

ELECTRICALLY CONDUCTIVE SUBSTANCE, METHOD OF PRODUCING ELECTRICALLY CONDUCTIVE SUBSTANCE, AND ELECTRODE, CATALYST AND MATERIAL CONTAINING ELECTRICALLY CONDUCTIVE SUBSTANCE

TECHNICAL FIELD

The present disclosure relates to an electrically conductive substance and a method of producing the electrically conductive substance. More specifically, the present disclosure relates to an electrically conductive substance which comprises a complex containing rubeanic acid ligands and copper ions, a method of producing the electrically conductive substance, and an electrode, a catalyst and a material which comprise the electrically conductive substance.

BACKGROUND

Non-aqueous secondary batteries (hereinafter also simply referred to as "secondary batteries") such as lithium ion secondary batteries are small and light, high in energy density, and capable of repeated cycles of charge and discharge. For such characteristics, secondary batteries are used in a wide variety of applications. In an effort to achieve higher performance of non-aqueous secondary batteries, developments of electrically conductive substances with high electrical conductivity have been extensively carried out.

For example, PTL 1 discloses, as a positive electrode active material for lithium ion batteries, a rubeanic acid-copper (II) complex, which is a metal organic complex of rubeanic acid (dithiooxamide) ligands and divalent copper ions (hereinafter also referred to as "copper (II) ions").

Rubeanic acid (dithiooxamide) is represented by the following chemical formula and the use of this compound even alone for non-aqueous secondary batteries has been studied due to its oxidation-reduction characteristics.

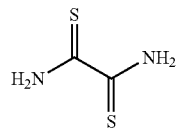

For example, PTL 2 discloses a lithium ion battery which comprises rubeanic acid or a rubeanic acid derivative as a positive electrode active material. PTL 3 discloses a fuel cell catalyst which comprises a rubeanic acid transition metal complex.

Recently, attention has been paid on coordination polymer complexes having a framework structure with regularly repeated nanopores with controlled size, where bifunctional or higher functional rigid organic ligands crosslink two or more metal ions by coordination bonding. Such coordination polymer complexes are also called metal-organic frameworks (MOFs) or porous coordination polymers (PCPs) and are expected to be used in a wide spectrum of applications.

CITATION LIST

Patent Literature

PTL 1: JPH0574458A
PTL 2: WO2013035829A1
PTL 3: JPS5857267A

SUMMARY

Technical Problem

However, most of the MOFs currently reported are insulators and only few have been reported to show electrical conductivity. Even MOFs which show electrical conductivity need to use uncommon special ligands and hence are not practical in terms of cost and supply. For this reason, there have been no reports of MOFs which are industrially utilized as electrically conductive substances.

On the other hand, if novel MOFs which show good electrical conductivity while having a common ligand can be successfully developed, they are expected to show superior charge-discharge characteristics due to their framework structure for use in non-aqueous secondary batteries as electrically conductive substances, as well as for use in a wide spectrum of applications.

For example, if a novel rubeanic acid-copper (I) complex of rubeanic acid ligands and copper (I) ions—a coordination polymer complex such as an MOF—can be obtained, due to its high copper (I) ion content, it is expected to have sufficiently improved conductivity, porosity, heat resistance, initial discharge characteristics and other properties compared to the rubeanic acid-copper (II) complex disclosed in PTL 1.

An object of the present disclosure is therefore to provide a novel electrically conductive substance comprising a novel rubeanic acid-copper (I) complex; a method of producing the electrically conductive substance; and an electrode, a catalyst and a material which comprise the electrically conductive substance.

Solution to Problem

The inventors conducted extensive studies to achieve the foregoing object and completed the present disclosure by establishing that an electrically conductive substance which comprises a complex containing rubeanic acid ligands and copper (I) ions can be obtained by reacting a rubeanic acid compound and a copper (I) compound in the presence of a base.

Specifically, the present disclosure aims to advantageously solve the foregoing problem and a disclosed electrically conductive substance comprises a complex containing rubeanic acid ligands and copper ions, wherein the copper ions comprise copper (I) ions. The disclosed electrically conductive substance is a novel electrically conductive substance which comprises a novel complex in which coordination bonds are formed between rubeanic acid ligands and copper (I) ions (hereinafter also referred to as a "rubeanic acid-copper (I) complex"), and has high electrical conductivity, high porosity, and high heat resistance. When a complex containing rubeanic acid ligands and copper (I) ions is called a "rubeanic acid-copper (I) complex" herein, it refers to a complex which at least contains coordination bonds formed between the rubeanic acid ligands and copper (I) ions. The "rubeanic acid-copper (I) complex" may contain an additional component other than the rubeanic acid ligands and copper (I) ions. The term "electrically conductive substance" as used herein refers to a substance having an electrical conductivity of $1.0 \times 10^{-7}$ S/cm or more. When used in chargeable/dischargeable electrochemical devices such as power storage devices and fuel cells, the disclosed electrically conductive substance can improve the device characteristics.

In the disclosed electrically conductive substance, the molar ratio of copper ion content to rubeanic acid ligand content is preferably 1.2 or more. At a molar ratio of 1.2 or more, it is possible to further increase the electrical conductivity and also improve the stability of the electrically conductive sub stance.

In the disclosed electrically conductive substance, the proportion of copper (I) ions in the copper ions is preferably 20 mol % or more. At a proportion of 20 mol % or more, it is possible to increase the electrical conductivity, porosity and heat resistance of the disclosed electrically substance.

The disclosed electrically conductive substance preferably has crystallinity. The presence of crystallinity indicates that the rubeanic acid-copper (I) complex contained in the disclosed electrically conductive substance is a coordination polymer complex having a regular framework structure analogous to an MOF, allowing the electrically conductive substance to have further increased electrical conductivity, porosity and heat resistance.

The phrase "has crystallinity" herein means that the electrically conductive substance has, when analyzed by powder X-ray diffraction, at least one diffraction peak having a full width at half maximum of 3° or less, not derived from the source compounds.

The disclosed electrically conductive substance preferably has a BET specific surface area of 20 $m^2$/g or more. With a BET specific surface area of 20 $m^2$/g or more, the electrically conductive substance can sufficiently function as a porous substance.

In the disclosed electrically conductive substance, the molar ratio of total copper ion content to rubeanic acid ligand content is preferably 2.0 or more. At a molar ratio of 2.0 or more, it is possible to further increase the heat resistance.

The electrically conductive substance preferably further comprises copper (I) sulfide and/or copper (II) sulfide. With copper (I) sulfide and/or copper (II) sulfide being further included, it is possible to further increase the electrical conductivity.

The disclosed method of producing an electrically conductive substance is a method of producing an electrically conductive substance which comprises a complex containing rubeanic acid ligands and copper ions, the method including mixing a rubeanic acid compound and a copper (I) compound in the presence of a base to provide an electrically conductive substance which comprises a complex containing rubeanic acid ligands and copper ions, wherein the copper ions comprise copper (I) ions.

With a rubeanic acid compound and a copper (I) compound being reacted in the presence of a base, it is possible to produce a novel electrically conductive substance which comprises the rubeanic acid-copper (I) complex, a novel complex.

In the disclosed method of producing an electrically conductive substance, the rubeanic acid compound and the base are preferably used in a molar ratio of 1:0.3 to 1:5. When the rubeanic acid compound and the base are used at a molar ratio of 1:0.3 to 1:5, it is possible to favorably produce the rubeanic acid-copper (I) complex.

In the disclosed method of producing an electrically conductive substance, the base is preferably at least one selected from the group consisting of alkali metal hydroxides, trialkylamines, and pyridines. Using such a base, it is possible to efficiently produce the rubeanic acid-copper (I) complex.

In the disclosed method of producing an electrically conductive substance, the copper (I) compound is preferably at least one selected from the group consisting of copper (I) chloride, copper (I) bromide, copper (I) iodide, copper (I) thiocyanate, copper (I) acetate, copper (I) sulfide, and copper (I) oxide. Using such a source copper (I) compound, it is possible to efficiently produce the rubeanic acid-copper (I) complex.

The disclosed electrode for a power storage device comprises the electrically conductive substance described above. With such an electrically conductive substance being included, the electrode provides excellent initial discharge characteristics.

The disclosed electrode for a fuel cell comprises the electrically conductive substance described above. With such an electrically conductive substance being included, the electrode provides excellent cell characteristics.

The disclosed catalyst comprises the electrically conductive substance described above. With such an electrically conductive substance being included, the catalyst can be suitably used as a catalyst for, for example, molecular conversion reactions.

The disclosed porous material comprises the electrically conductive substance described above. With such an electrically conductive substance being included, the porous material can efficiently adsorb and/or desorb gas molecules.

Advantageous Effect

According to the present disclosure, it is possible to provide a novel electrically conductive substance which comprises the novel rubeanic acid-copper (I) complex and which has high electrical conductivity, high porosity and high heat resistance and also improves, when used for the manufacture of an electrochemical device, initial discharge characteristics of the device.

According to the present disclosure, it is also possible to provide a method of producing a novel electrically conductive substance which comprises the novel rubeanic acid-copper (I) complex and which has high electrical conductivity, high porosity and high heat resistance and also improves, when used for the manufacture of an electrochemical device, initial discharge characteristics of the device.

According to the present disclosure, it is also possible to provide an electrode, a catalyst and a material which comprise the electrically conductive substance containing the novel rubeanic acid-copper (I) complex described above and which may show improved performance.

DETAILED DESCRIPTION

Figure 1:
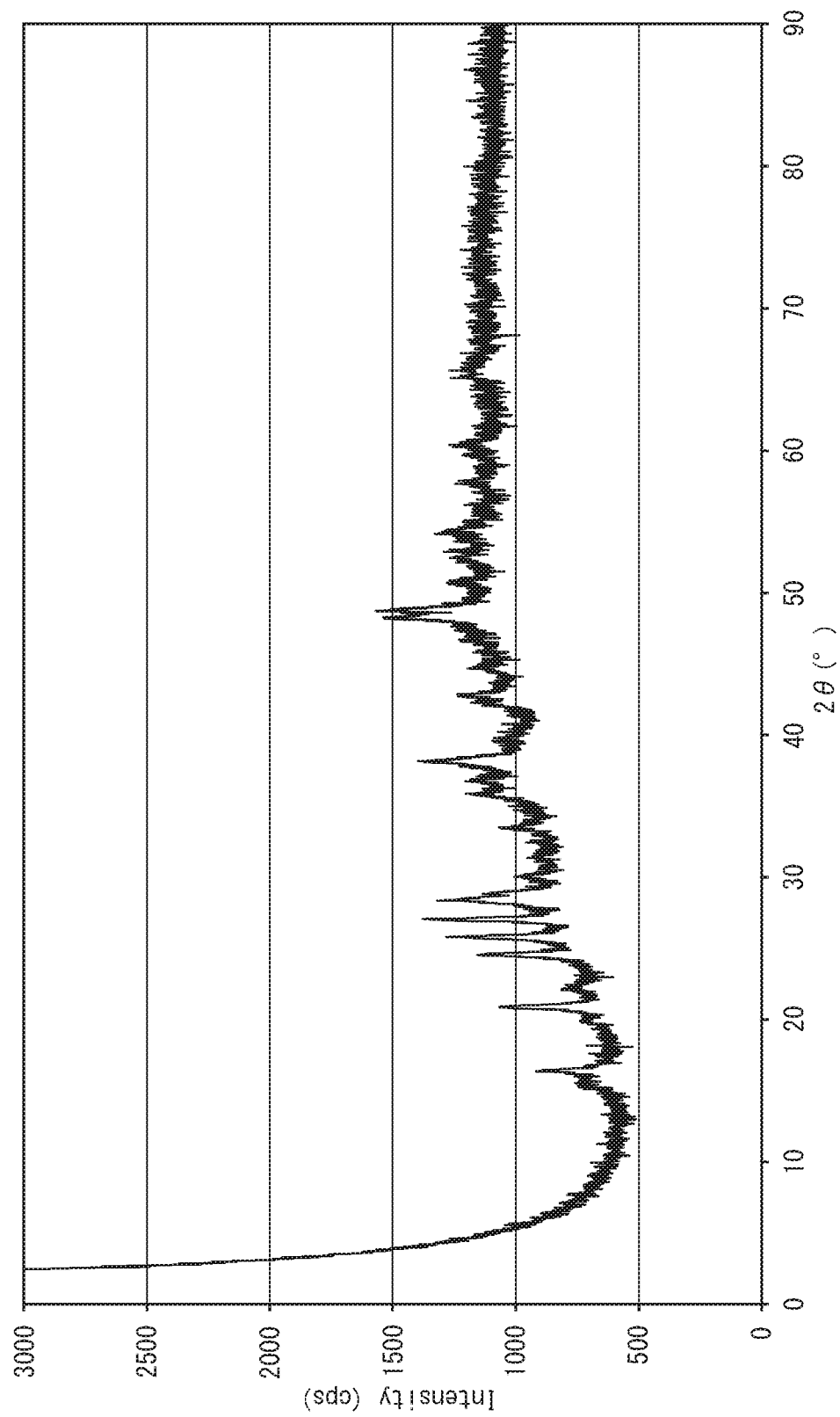
FIG. 1 is a powder X-ray diffraction chart of an electrically conductive substance obtained in Example 1.

The present disclosure will be described in detail below based on embodiments.

(Electrically Conductive Substance)

The disclosed electrically conductive substance comprises a complex containing rubeanic acid ligands and copper ions, wherein the copper ions comprise copper (I) ions. Specifically, the disclosed electrically conductive substance comprises a rubeanic acid-copper (I) complex, a novel complex which shows electrical conductivity, where coordination bonds are formed between rubeanic acid ligands and copper (I) ions.

The rubeanic acid-copper (I) complex is a novel compound in which a rubeanic acid ligand is coordinated to a copper (I) ion as the core metal ion.

The inventors identified that the produced novel compound is identical to the disclosed electrically conductive substance by confirming that: powder X-ray diffraction and IR analysis of the compound yielded a powder X-ray diffraction chart and an IR analysis chart, respectively, which are different from those of the rubeanic acid-copper (II) complex and any other known compounds; the nitrogen atoms and sulfur atoms of a rubeanic acid ligand are coordinated to copper ions; copper (I) ions are included in the compound; the rubeanic acid ligands and copper ions are included at a molar ratio of greater than 1:1; and so forth.

The disclosed electrically conductive substance will now be described below.

Methods of identifying the rubeanic acid-copper (I) complex are described later.

The disclosed electrically conductive substance preferably comprises rubeanic acid ligands and copper ions at a molar ratio of 1:1.2 or more. In other words, in the disclosed electrically conductive substance, the molar ratio of copper ion content to rubeanic acid ligand content is preferably 1.2 or more. At a molar ratio of copper ion content to rubeanic acid ligand content of 1.2 or more, it is possible to increase the electrical conductivity and stability of the substance.

The term "copper ion content" as used herein refers to a total content of all the copper ion species contained in the disclosed electrically conductive substance, i.e., copper (I) ions (monovalent copper ions) plus copper (II) ions (divalent copper ions).

The rubeanic acid-copper (II) complex consisting only of copper (II) ions and rubeanic acid ligands (hereinafter referred to as a "pure rubeanic acid-copper (II) complex"), where rubeanic acid ligands are coordinated to copper (II) ions, contains rubeanic acid ligands and copper (II) ions at a stoichiometric molar ratio of 1:1. In other words, in the pure rubeanic acid-copper (II) complex, the stoichiometric molar ratio of copper ion content to rubeanic acid ligand content is 1.

On the other hand, the rubeanic acid-copper (I) complex consisting only of copper (I) ions and rubeanic acid ligands (hereinafter referred to as a "pure rubeanic acid-copper (I) complex"), where rubeanic acid ligands are coordinated to copper (I) ions, contains rubeanic acid ligands and copper (I) ions at a stoichiometric molar ratio of 1:2. In other words, in the pure rubeanic acid-copper (I) complex, the stoichiometric molar ratio of copper ion content to rubeanic acid ligand content is 2.

However, copper (I) ions are less stable than copper (II) ions and may be easily oxidized to copper (II) ions.

Thus, in practice, some of the copper ions (I) in the source compound may be oxidized to copper (II) ions during the synthesis of the rubeanic acid-copper complex, resulting in the synthesized complex having a mixed presence of coordination bonds formed between rubeanic acid ligands and copper (I) ions and coordination bonds formed between rubeanic acid ligands and copper (II) ions. Such a complex may also be referred to as a "rubeanic acid-copper mixed valence complex." The molar ratio of copper ion content (i.e., total content of copper (I) ions (monovalent copper ions) plus copper (II) ions (divalent copper ions)) to rubeanic acid ligand content in the rubeanic acid-copper mixed valence complex is greater than 1 and less than 2.

Specifically, a molar ratio of copper ion content to rubeanic acid ligand content of 1.2 or more in a complex containing rubeanic acid ligands and copper ions means that the complex contains an amount of coordination bonds formed between the rubeanic acid ligands and copper ions to an extent that may further increase the electrical conductivity and stability of the complex as an electrically conductive substance, and may also optionally contain coordination bonds formed between the rubeanic acid ligands and copper (II) ions.

Thus, the disclosed electrically conductive substance may be a "pure rubeanic acid-copper (I) complex" consisting only of rubeanic acid ligands and copper (I) ions; a "rubeanic acid-copper mixed valence complex" containing rubeanic acid ligands, copper (I) ions, and copper (II) ions; or a mixture thereof. The disclosed electrically conductive substance may also comprise a complex which contains, in addition to rubeanic acid ligands, copper (I) ions and copper (II) ions, other components such as base-derived components that may be unavoidably mixed during the production process. In other words, the disclosed electrically conductive substance is not limited to a particular one as long as it comprises a complex containing coordination bonds formed between rubeanic acid ligands and copper (I) ions; the disclosed electrically conductive substance may comprise a complex which contains copper (II) ions and other components. A complex which contains coordination bonds formed between rubeanic acid ligands and copper (I) ions and may show electrical conductivity as described above is collectively referred to as a "rubeanic acid-copper (I) complex" herein.

From the perspective of the frequency of coordination bonds formed between rubeanic acid ligands and copper (I) ions in the disclosed electrically conductive substance, the molar ratio of copper ion content to rubeanic acid ligand content in the electrically conductive substance is more preferably 1.3 or more, even more preferably 1.5 or more, still even more preferably 1.7 or more, and particularly preferably 1.9 or more. At a molar ratio of copper ion content to rubeanic acid ligand content of 1.3 or more, it is speculated that the electrically conductive substance may have a sufficiently high frequency of coordination bonds formed between rubeanic acid ligands and copper (I) ions.

From the perspective of the heat resistance of the disclosed electrically conductive substance, the molar ratio of copper ion content to rubeanic acid ligand content in the electrically conductive substance is more preferably 2.0 or more, even more preferably greater than 2.0, and still even more preferably 4.0 or more. At a molar ratio of copper ion content to rubeanic acid ligand content of 2.0 or more, it is possible to increase heat resistance. Further, from the perspective of synthesis yield, the molar ratio of copper ion content to rubeanic acid ligand content in the electrically conductive substance is preferably 10.0 or less, more preferably 8.0 or less, and even more preferably 6.0 or less.

The reason why heat resistance in particular can be improved at a molar ratio of copper ion content to rubeanic acid ligand content of greater than 2.0 is unclear. It is speculated that improved heat resistance is achieved because the copper (I) ions are present in an excessive of the stoichiometric equivalent ratio and hence form clusters in the rubeanic acid-copper (I) complex.

The copper ion content relative to the rubeanic acid ligand content in the rubeanic acid-copper (I) complex-containing electrically conductive substance can be obtained by any of the methods known in the art, e.g., by the method as will be described below.

First, mass spectrometry is performed on the electrically conductive substance to confirm the presence of rubeanic acid ligands. Specifically, a mass spectrum is measured to confirm the presence of a fragment peak at mass number 118 assigned to rubeanic acid ligand. Depending on the state of the complex and the measurement conditions, the peak may be observed at mass number 119 or 120. When a rubeanic acid ligand having a substituent is included, a fragment peak at mass number assigned to rubeanic acid ligand including a substituent may be confirmed instead.

Subsequently, thermogravimetric-differential thermal analysis (TG-DTA) is performed under a nitrogen stream, where weight loss on heating is measured by heating the substance to 600° C. at a temperature elevation rate of 10° C./min. With the ash taken as copper (I) sulfide, the molar ratio of copper (I) ion content to rubeanic acid content can be calculated.

In the disclosed electrically conductive substance, preferably, 20 mol % or more of the copper ions are copper (I) ions, and more preferably, 40 mol % or more of the copper ions are copper (I) ions. With 20 mol % or more of the copper ions (total of copper (I) ions and copper (II) ions) being copper (I) ions, the electrical conductivity, porosity and heat resistance of the electrically conductive substance may be increased.

The proportion of copper (I) ions in the copper ions in the electrically conductive substance can be found by performing an X-ray absorption near edge structure (XANES) analysis, superimposing the chart obtained from the analyte sample with those obtained from standard samples, and performing fitting. The standard samples used here are copper foil, copper (I) oxide, copper (II) oxide, copper (I) sulfide, and copper (II) sulfide.

As described above, the disclosed electrically conductive substance only needs to comprise the rubeanic acid-copper (I) complex. The electrically conductive substance may comprise one or more types of other compound(s) as an optional component other than the complex containing rubeanic acid ligands and copper (I) ions.

Compounds as an optional component are not limited to particular ones and examples thereof include by-products produced in the production process of the rubeanic acid-copper (I) complex.

For example, the disclosed electrically conductive substance preferably further contains copper (I) sulfide and/or copper (II) sulfide. With copper (I) sulfide and/or copper (II) sulfide being included, conductivity can be further improved. The copper (I) sulfide content and/or the copper (II) sulfide content can be determined as appropriate.

[Identification of Rubeanic Acid-Copper (I) Complex]

Hereinafter, as an exemplary method of identifying the rubeanic acid-copper (I) complex, comparison with known compounds by powder X-ray diffraction and IR analysis and detection of coordination bonds by extended X-ray absorption fine structure (EXAFS) analysis are explained.

Identification of the rubeanic acid-copper (I) complex is not limited to the particular method described below and can be carried out using analysis techniques known in the art, either alone or in combination.

Examples of powder X-ray diffraction charts measured for an electrically conductive substance according to one embodiment of the present disclosure are shown in FIGS. 1, 3, 5 and 6.

The powder X-ray diffraction charts of the disclosed electrically conductive substance have a distinctive difference from those of the rubeanic acid-copper (II) complex. For example, in the powder X-ray diffraction charts of the disclosed electrically conductive substance, as shown in FIGS. 1, 3, 5 and 6, diffraction peaks having a full width at half maximum of not greater than 3°, which are not derived from the source compounds, are detected at diffraction angles (2θ) of around 22° and around 28°.

Figure 10:
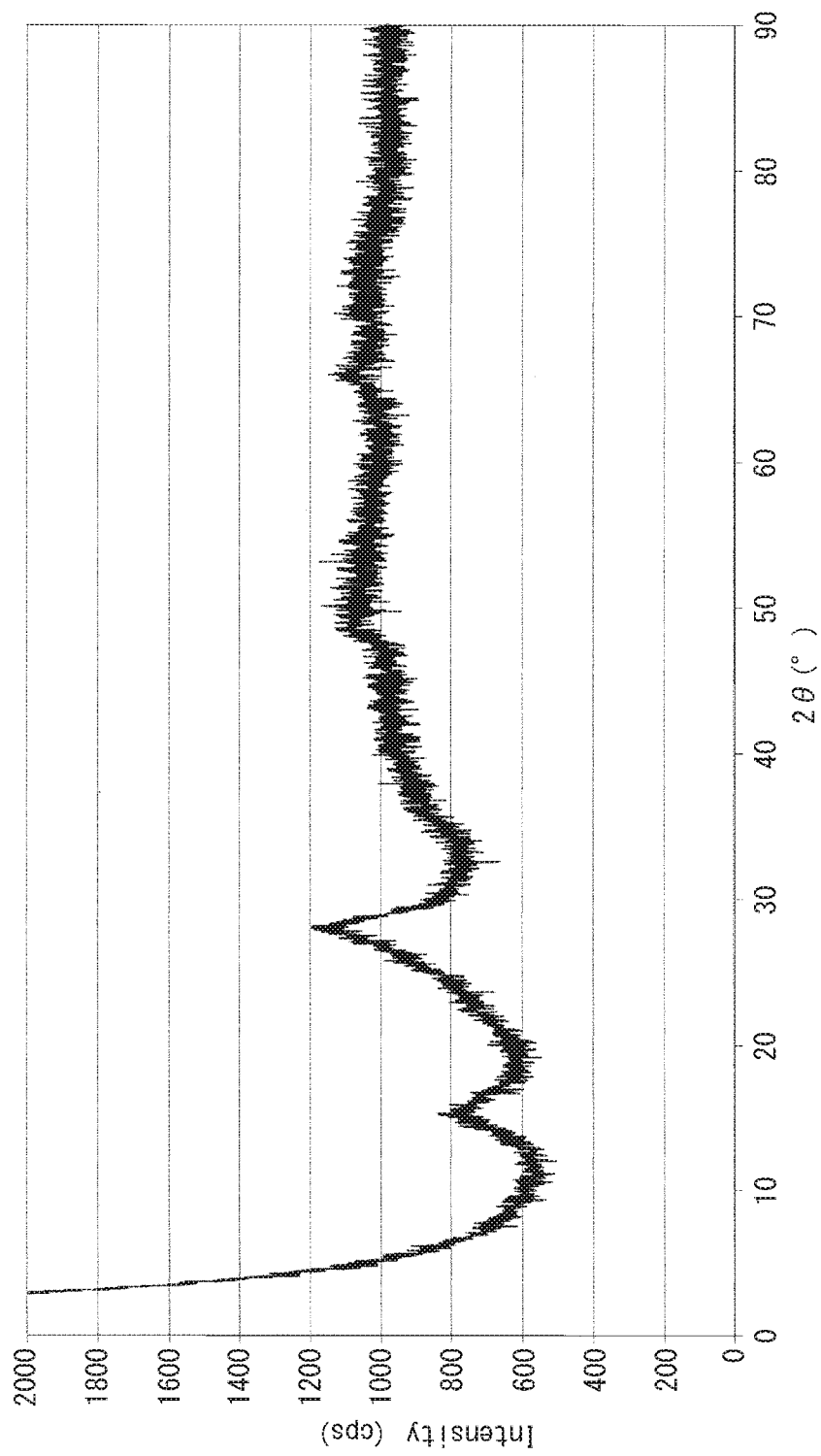
FIG. 10 is a powder X-ray diffraction chart of an electrically conductive substance (rubeanic acid-copper (II) complex) obtained in Comparative Example 2.

On the other hand, in the powder X-ray diffraction chart of the rubeanic acid-copper (II) complex shown in FIG. 10, no diffraction peak is detected that has a full width at half maximum of not greater than 3°, suggesting that the diffraction peak is broad and the complex is amorphous.

Figure 12:
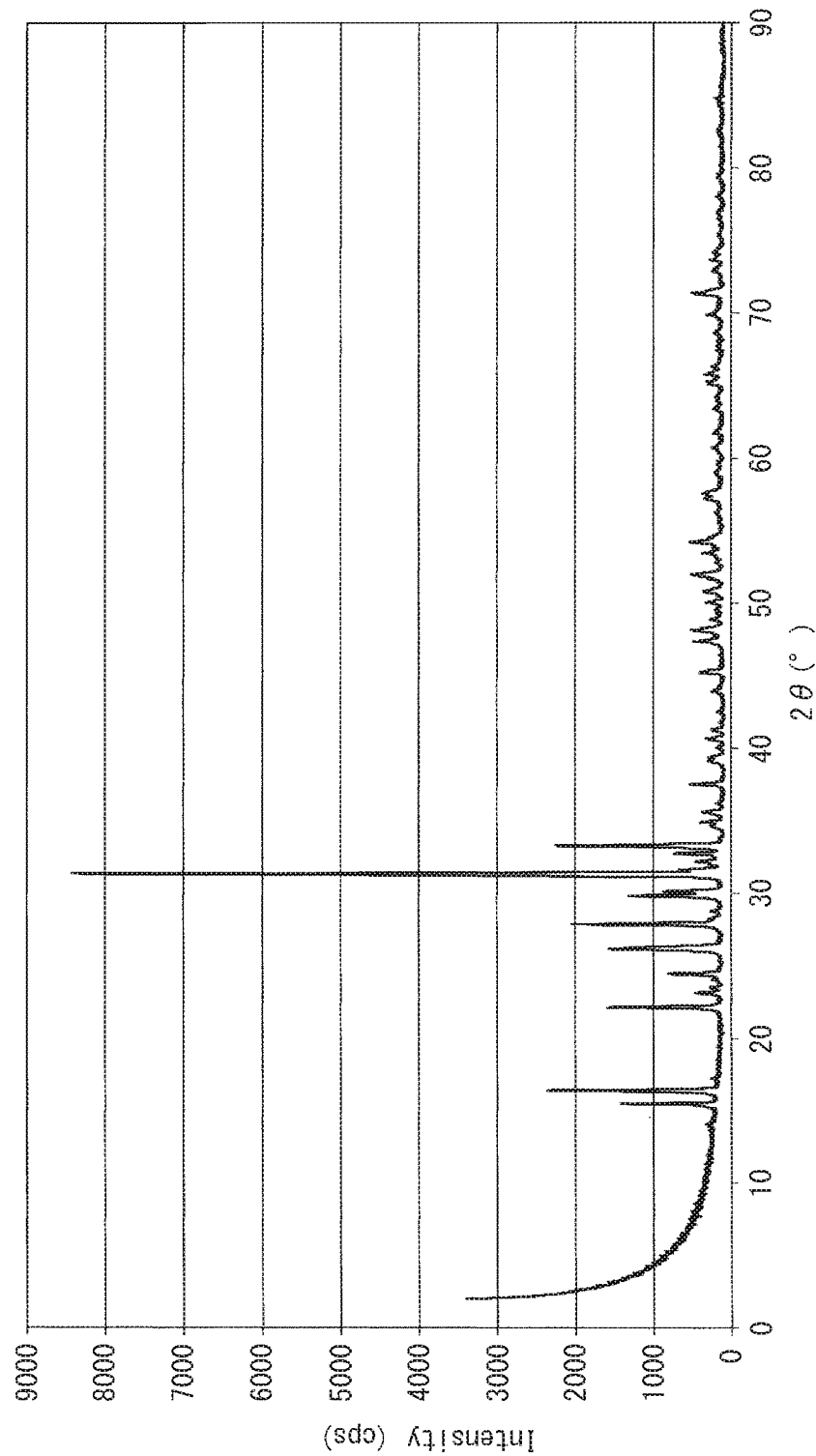
FIG. 12 is a powder X-ray diffraction chart of rubeanic acid.

Naturally, the powder X-ray diffraction chart of the disclosed electrically conductive substance also has a distinctive difference from that of rubeanic acid, a source of the disclosed electrically conductive substance (hereinafter also referred to as "source rubeanic acid"). For reference, a powder X-ray diffraction chart of source rubeanic acid is shown in FIG. 12.

Figure 2:
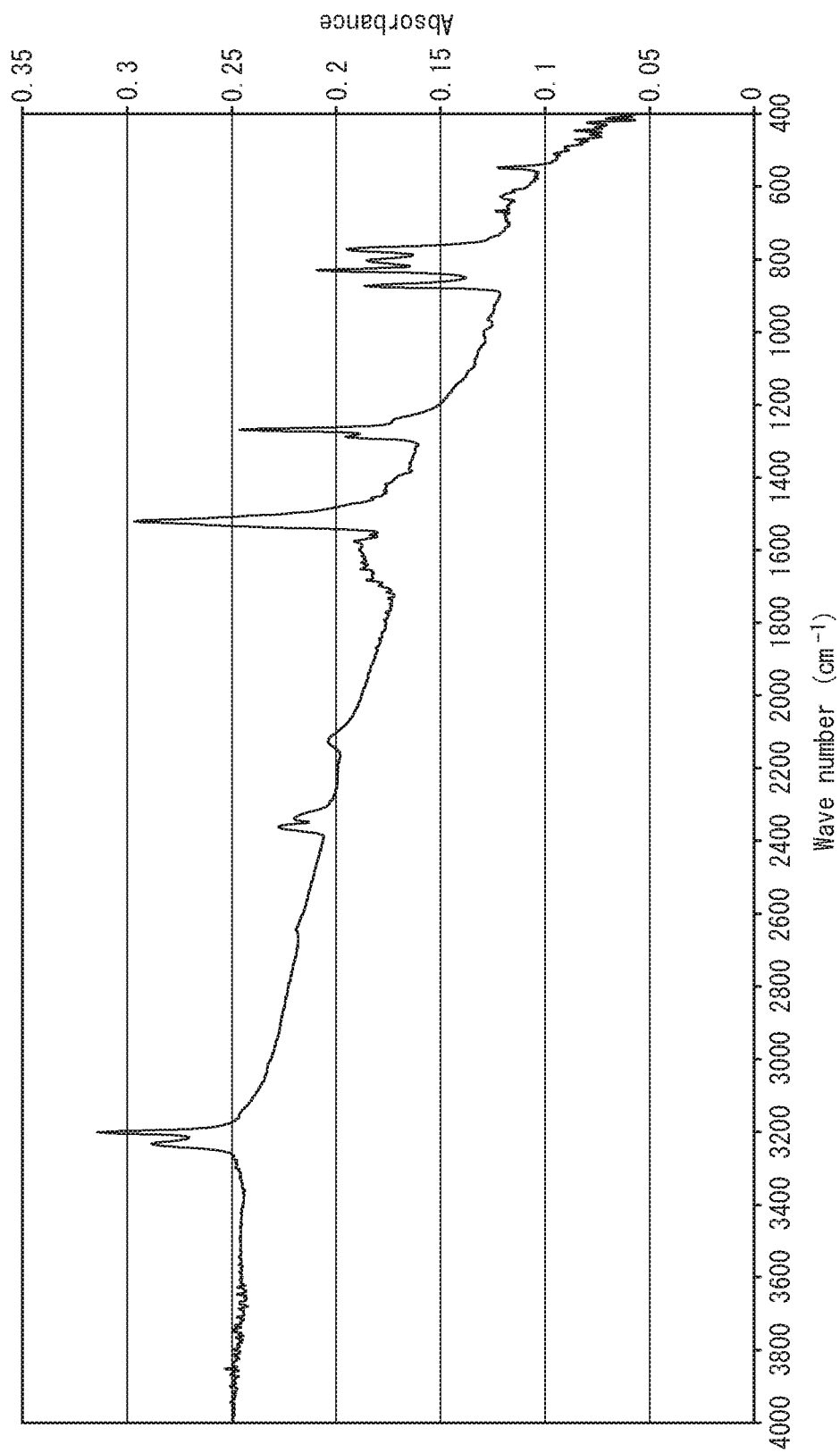
FIG. 2 is an IR analysis chart of an electrically conductive substance obtained in Example 1.
Figure 4:
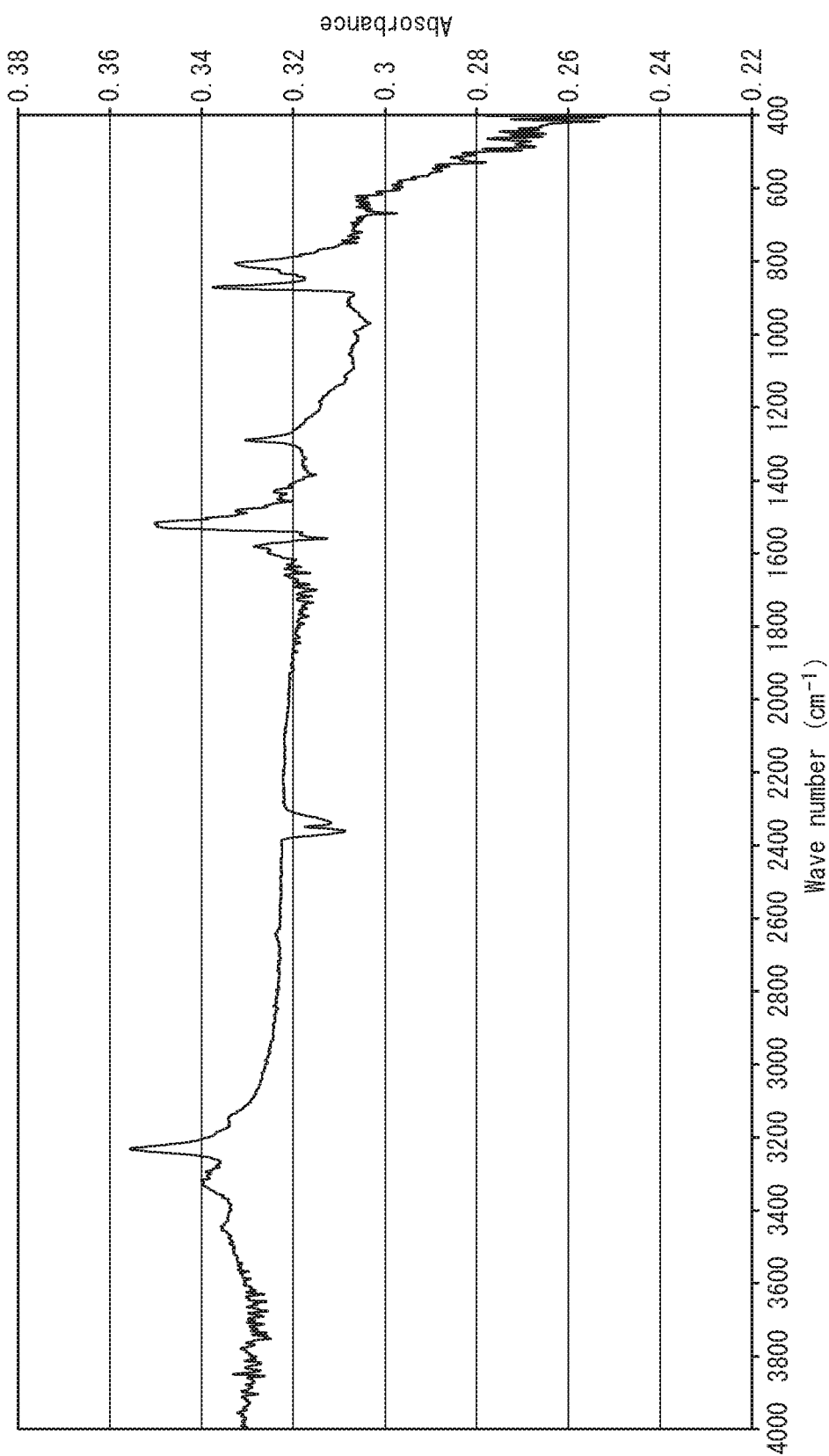
FIG. 4 is an IR analysis chart of an electrically conductive substance obtained in Example 2.
Figure 7:
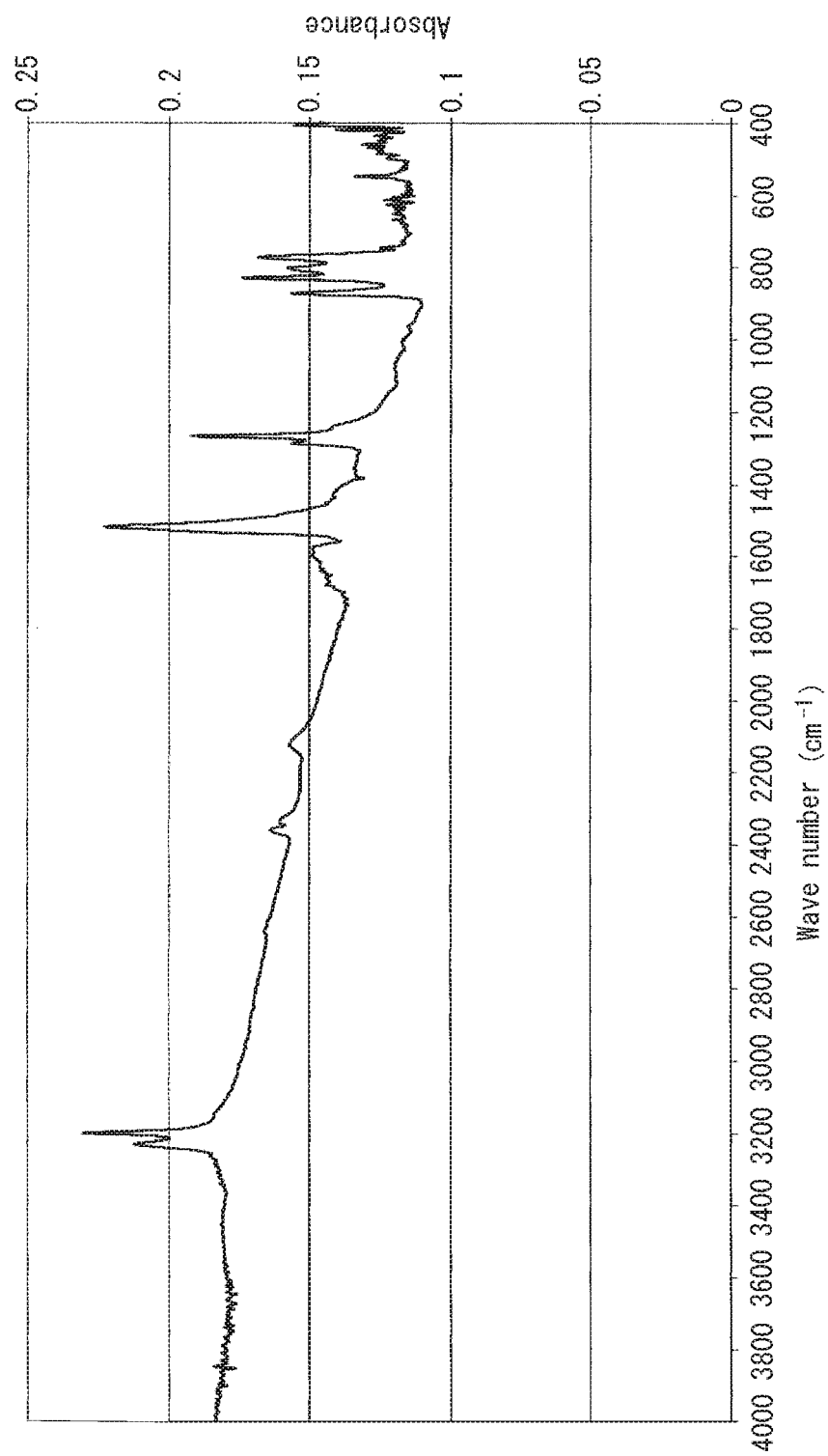
FIG. 7 is an IR analysis chart of an electrically conductive substance obtained in Example 4.
Figure 13:
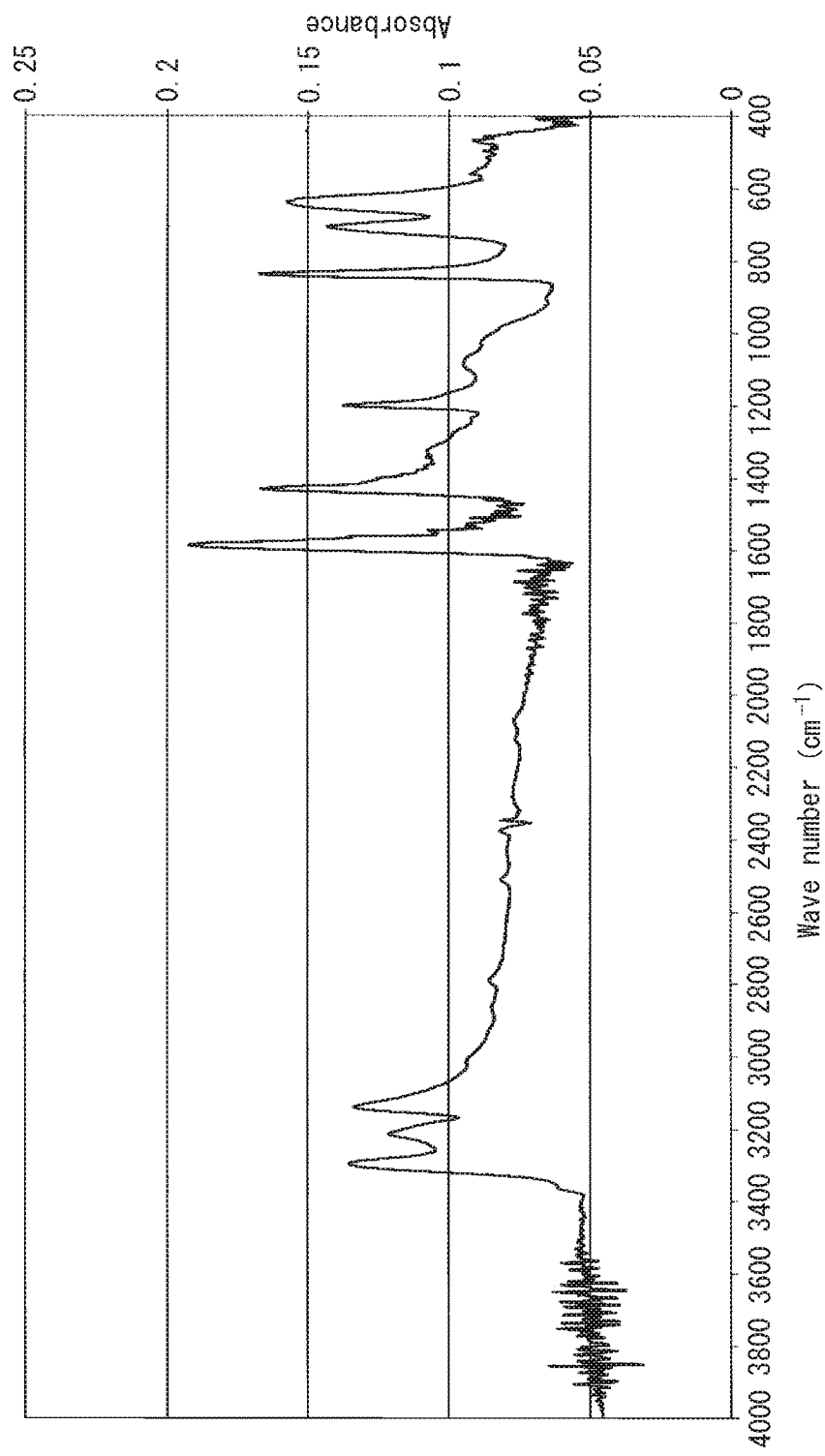
FIG. 13 is an IR analysis chart of rubeanic acid.

Examples of IR analysis charts measured for the electrically conductive substance according to one embodiment of the present disclosure are shown in FIGS. 2, 4 and 7. For reference, an IR analysis chart of source rubeanic acid is shown in FIG. 13.

Figure 11:
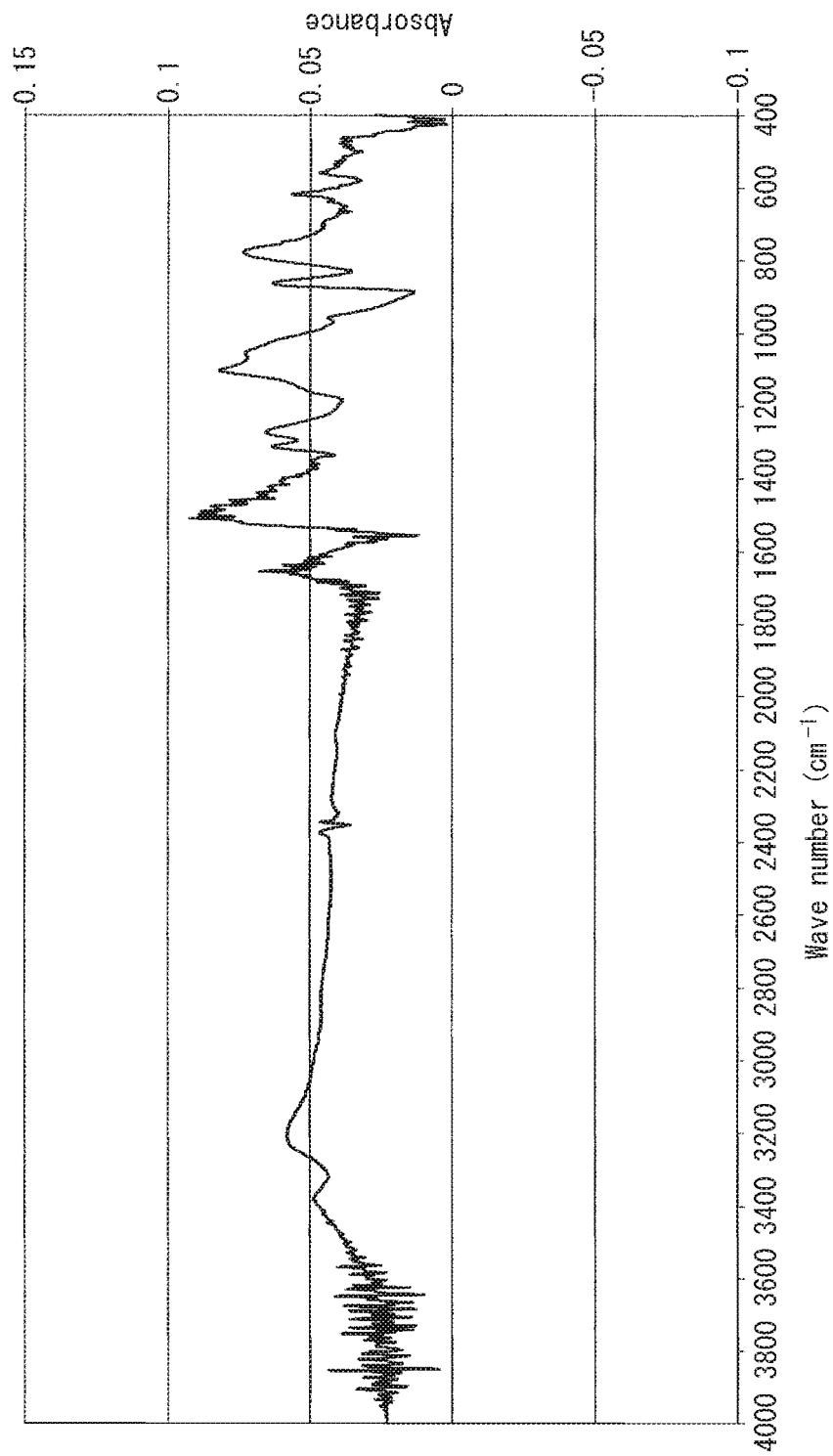
FIG. 11 is an IR analysis chart of an electrically conductive substance (rubeanic acid-copper (II) complex) obtained in Comparative Example 2.

The IR analysis chart of the disclosed electrically conductive substance has a distinctive difference from that of the rubeanic acid-copper (II) complex. For example, in the IR analysis charts of the disclosed electrically conductive substance shown in FIGS. 2, 4, and 7, three characteristic infrared absorption peaks derived from the $NH_2$ group of source rubeanic acid (hereinafter also referred to as "peaks derived the source rubeanic acid's $NH_2$ group"), observed at a wavenumber of around 3200 $cm^{-1}$ on the IR analysis chart of the source rubeanic acid shown in FIG. 13, have disappeared. This reveals that the source rubeanic acid has been consumed. The same applies to the IR analysis chart of the divalent rubeanic acid-copper (II) complex shown in FIG. 11.

Figure 9:
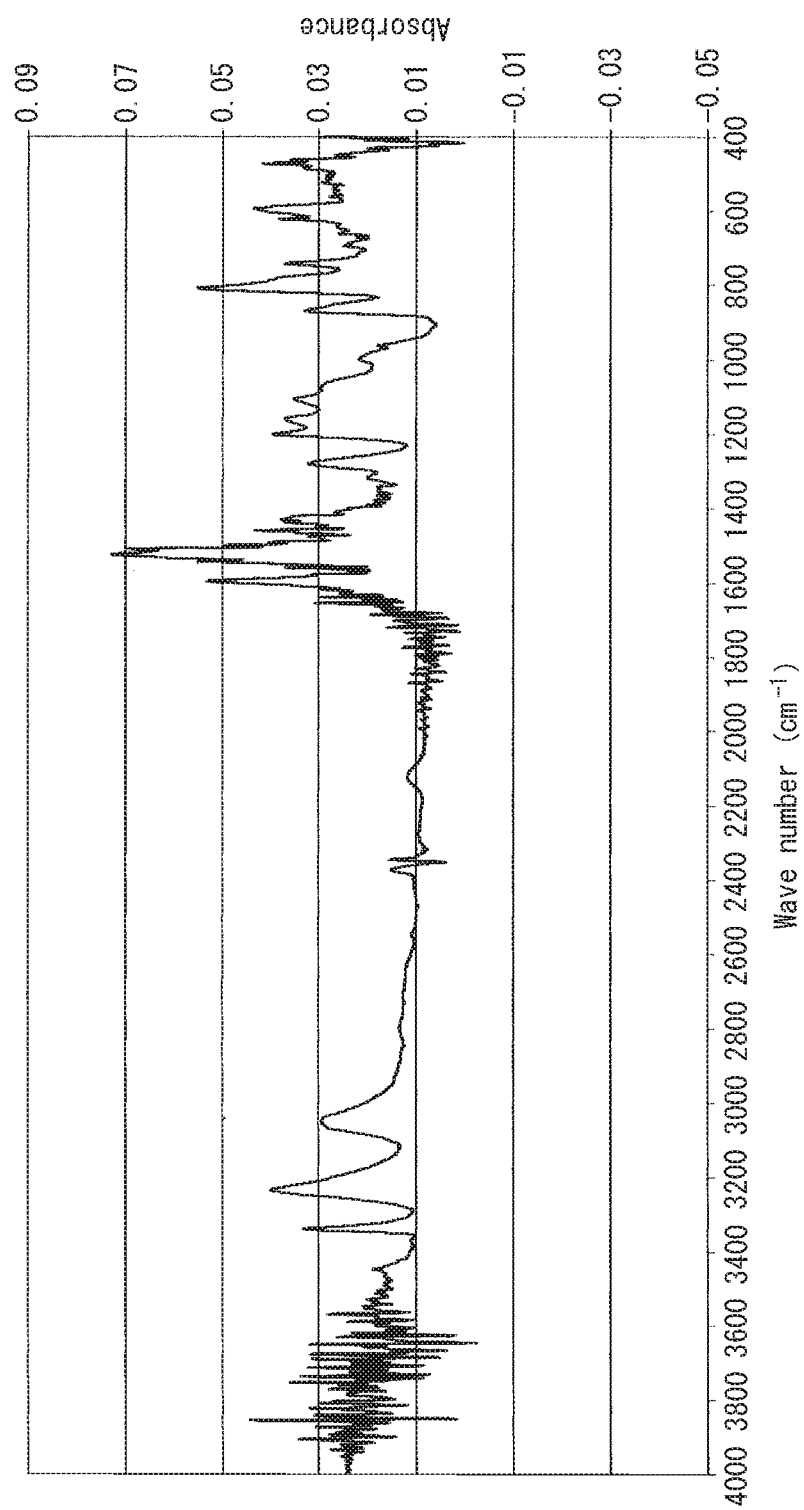
FIG. 9 is an IR analysis chart of a substance (rubeanic acid-copper (I) chloride complex) obtained in Comparative Example 1.

On the other hand, in the IR analysis chart of the rubeanic acid-copper (I) chloride complex (FIG. 9), wavenumber shift is observed, but three infrared absorption peaks at a wavenumber of around 3200 cm$^{-1}$ ("peaks derived the source rubeanic acid's NH$_2$ group) remains, suggesting that the NH$_2$ structure of source rubeanic acid is maintained.

The fact that the nitrogen atoms and sulfur atoms of a rubeanic acid ligand are coordinated to copper ions in the disclosed electrically conductive substance can be confirmed (detected) by extended X-ray absorption fine structure (EXAFS) analysis. The closest atom, i.e., the coordinating atom, can be determined from a comparison between the measured data and the simulation result obtained when the closest atom is assumed to be sulfur or nitrogen.

The structure of the rubeanic acid-copper (I) complex contained in the disclosed electrically conductive substance has not yet been characterized in detail. However, the complex is assumed to be a coordination polymer complex having a regular framework structure in which each of the four donor atoms (two nitrogen atoms and two sulfur atoms) of one rubeanic acid ligand three-dimensionally crosslinks separate copper (I) ions.

The rubeanic acid ligands in the rubeanic acid-copper (I) complex may not have a substituent or may have a substituent on one or both of the nitrogen atoms. Further, the rubeanic acid-copper (I) complex may contain a rubeanic acid ligand having no substituent and a rubeanic acid ligand having a substituent.

Examples of substituents on the rubeanic acid ligand include a linear or branched C1-C3 alkyl.

[Physical Properties]

Hereinafter, the physical properties of the disclosed electrically conductive substance will be described.

As demonstrated in Examples described later, for all of electrical conductivity, porosity, initial discharge characteristics and heat resistance described below, the disclosed electrically conductive substance has excellent physical property values that are significantly higher than those of the rubeanic acid-copper (I) chloride complex and rubeanic acid-copper (II) complex, as well as has crystallinity.

—Electrical Conductivity—

The disclosed electrically conductive substance has high electrical conductivity.

The electrical conductivity of the disclosed electrical conductive substance is not limited to a particular value, but preferably has an electrical conductivity of $1.0 \times 10^{-5}$ S/cm or more, more preferably $4.0 \times 10^{-5}$ S/cm or more, and even more preferably $2.0 \times 10^{-4}$ S/cm or more. When the electric conductivity is $1.0 \times 10^{-5}$ S/cm or more, it is sufficient for use as an electric conductor.

The electrical conductivity of the electrically conductive substance can be measured by the four-point probe method.

—Porosity—

The disclosed electrically conductive substance preferably has a BET specific surface area of 20 m$^2$/g or more, more preferably 60 m$^2$/g or more, even more preferably 90 m$^2$/g or more, and particularly preferably 120 m$^2$/g or more. When the BET specific surface area is 20 m$^2$/g or more, the electrically conductive substance may favorably function as a porous substance.

"BET specific surface area" refers to a nitrogen adsorption specific surface area as measured by the BET method.

—Crystallinity—

The disclosed electrically conductive substance preferably has crystallinity. The presence of crystallinity indicates that the rubeanic acid-copper (I) complex is a coordination polymer complex having a regular crystalline structure, allowing the substance to have further improved electrical conductivity, porosity and heat resistance.

The phrase "has crystallinity" herein means that, when analyzed by powder X-ray diffraction, at least one diffraction peak is observed that has a full width at half maximum (FWHM) of 3° or less, not derived from the source compounds.

From the perspective of higher crystallinity and higher purity, the full width at half maximum (FWHM) is preferably less than 3°, more preferably 2.5° or less, and even more preferably 2° or less. Full width at half maximum (FWHM) refers to a full width of a diffraction peak at a half of the maximum of the peak.

—Initial Discharge Characteristics—

When used to manufacture an electrochemical device, the disclosed electrically conductive substance can improve the initial discharge capacity of the electrochemical device.

A non-aqueous secondary battery, an electrochemical device manufactured using the disclosed electrically conductive substance, preferably has an initial discharge capacity of 250 mAh/g or more, and more preferably 300 mAh/g or more, as measured for example at room temperature within a potential range of 4.4 to 0.5 V (Li/Li$^+$) at a constant current of 20 mA/g. When the electrochemical device as a non-aqueous secondary battery has an initial discharge capacity of 250 mAh/g or more as measured under the above conditions, it is sufficient for practical use. Thus, the disclosed electrical conductive substance can sufficiently function as an active material of an electrochemical device such as a non-aqueous secondary battery.

—Heat Resistance—

The disclosed electrically conductive substance has excellent heat resistance. Heat resistance can be evaluated using, as an index, a 5% weight loss temperature as measured by thermogravimetric analysis under an inert atmosphere or at reduced pressure.

The heat resistance index of the disclosed electrically conductive substance is not limited to a particular value, but the 5% weight loss temperature under an inert atmosphere or at reduced pressure is preferably 200° C. or higher, and more preferably 210° C. or higher. When the 5% weight loss temperature at a temperature elevation rate of 10° C./min is 200° C. or higher, the electrically conductive substance can be suitably used as an active material of a power storage device or as an electrode catalyst of a fuel cell.

[Applications]

Hereinafter, non-limiting examples of applications of the disclosed electrically conductive substance will be described.

—Power Storage Device—

For its high electrical conductivity, high porosity and high heat resistance, the disclosed electrically conductive substance can be suitably used as an active material of power storage devices such as non-aqueous secondary batteries and capacitors.

The power storage device in which the disclosed electrically conductive substance can be used is not limited to a particular one and examples thereof include non-aqueous secondary batteries such as lithium ion batteries (LIBs), sodium ion batteries (SIBs), magnesium ion batteries (MgIBs), and aluminum ion batteries (AlIBs); and capacitors such as electric double layer capacitors (EDLCs), and lithium ion capacitors (LICs).

—Fuel Cell—

For its high electrical conductivity, high porosity and high heat resistance, the disclosed electrically conductive substance can be suitably used also as an electrode catalyst of a fuel cell.

The fuel cell in which the disclosed electrically conductive substance can be used is not limited to a particular one and examples thereof include polymer electrolyte fuel cells (PEFCs), phosphoric acid fuel cells (PAFCs), molten carbonate fuel cells (MCFCs), and solid oxide fuel cells (SOFCs).

—Catalyst—

Because the disclosed electrically conductive substance contains ions of Cu (I)—a transition metal—in addition to having porosity and heat resistance, it can be suitably included in a catalyst.

The catalyst which comprises the disclosed electrically conductive substance is not limited to a particular one and can be suitably used as a molecular conversion catalyst for, for example, a $CO_2$ reduction reaction, an alcohol oxidation reaction, and an oxygen reduction reaction.

—Porous Material—

Because the disclosed electrically conductive substance has porosity, it can be suitably included in a porous material that may function as a gas adsorption (storage) agent or gas separation agent.

The gas that can be adsorbed or separated using a porous material which comprises the electrically conductive substance is not limited to a particular one and examples thereof include hydrocarbons, $N_2$, $O_2$, $H_2$, CO and $CO_2$.

(Method of Producing Electrically Conductive Substance)

The disclosed method of producing an electrically conductive substance comprises reacting a rubeanic acid compound and a copper (I) compound in the presence of a base to provide an electrically conductive substance which comprises a complex containing rubeanic acid ligands and copper ions. The complex containing rubeanic acid ligands and copper ions, obtained by such a step, is a rubeanic acid-copper (I) complex such as that described above.

The rubeanic acid-copper (II) complex disclosed in PTL 1 and most of the MOFs currently reported are easily synthesized because continuous coordination bonding occurs by simply mixing a ligand compound and metal ions in solvent.

However, the rubeanic acid-copper (I) complex could not be obtained by simply mixing a rubeanic acid compound and copper (I) ions in solvent.

The inventors found for the first time that an electrically conductive substance which comprises a rubeanic acid-copper (I) complex can be obtained by reacting a rubeanic acid compound and a copper (I) compound in the presence of a base.

[Base]

Examples of bases include alkali metal hydroxides such as lithium hydroxide, sodium hydroxide, and potassium hydroxide; trialkylamines such as trimethylamine and triethylamine; and pyridines. Preferred are lithium hydroxide, sodium hydroxide, potassium hydroxide, trimethylamine, and triethylamine, with lithium hydroxide, sodium hydroxide, and potassium hydroxide being more preferred. These bases may be hydrates. Further, these bases may be used singly or in combination.

[Rubeanic Acid Compound]

Examples of rubeanic acid compounds include rubeanic acid having no substituent (i.e, dithiooxamide) and rubeanic acid having a linear or branched C1-C3 alkyl on one or both of the nitrogen atoms. These rubeanic acid compounds may be used singly or in combination.

The amounts of the base and the rubeanic acid compound used are not limited to particular values but the molar ratio of rubeanic acid compound to base is preferably 1:0.3 to 1:5, more preferably 1:0.5 to 1:4.5, and even more preferably 1:1 to 1:4. When the molar ratio of rubeanic acid compound to base falls within the above range, it is possible to efficiently obtain the disclosed electrically conductive substance which comprises the rubeanic acid-copper (I) complex.

Increases in the amount of the base used within the range described above promotes the decomposition reaction of the rubeanic acid compound, so that copper (I) sulfide and/or copper (II) sulfide are produced as by-products. As to the amount of the base used for producing copper (I) sulfide and/or copper (II) sulfide as by-products, the molar ratio of rubeanic acid compound to base is set to 1:1.7 to 1:5, for example.

[Copper (I) Compound]

Examples of copper (I) compounds include salts containing copper (I) ions, such as copper (I) chloride, copper (I) bromide, copper iodide (I), copper (I) thiocyanate, copper (I) acetate, copper (I) sulfide, and copper (I) oxide (I). Preferred are copper (I) chloride, copper (I) acetate, and copper (I) thiocyanate. These copper (I) compounds may be used singly or in combination.

The amount of the copper (I) compound used is not limited to a particular value and only needs to be adjusted as appropriate according to the desired amount of the rubeanic acid-copper (I) complex in the electrically conductive substance such that the molar ratio of rubeanic acid compound to copper (I) compound is 1:1 to 1:4.

By performing the steps described below using a base, a rubeanic acid compound, and a copper (I) compound such as those described above, it is possible to obtain the disclosed electrically conductive substance which comprises the rubeanic acid-copper (I) complex.

The production of the electrically conductive substance may be performed under an inert gas atmosphere or at reduced pressure in a closed system, or may be performed in the presence of air in an open system. For example, when all the steps described below are performed in a closed system under an inert gas (e.g., argon or nitrogen gas) atmosphere or at reduced pressure, it is possible to obtain an electrically conductive substance composed of a rubeanic acid-copper (I) complex in which almost all the components are copper (I) ions and rubeanic acid ligands (i.e., a complex quite analogous to the "pure rubeanic acid-copper (I) complex" described above). On the other hand, when some or all of the steps described below are performed in the presence of air in an open system, it is possible to obtain an electrically conductive substance which comprises the "rubeanic acid-copper mixed valence complex" described above. Thus, it is possible to obtain an electrically conductive substance which comprises a complex having a desired composition by appropriately performing the steps of the production process in a closed system and/or an open system.

<Pre-Mixing Step>

In the disclosed method of producing an electrically conductive substance, optionally, the rubeanic acid compound and the base may be mixed in advance prior to the step of mixing the rubeanic acid compound and the copper (I) compound. By mixing the rubeanic acid compound and the base in advance, the rubeanic acid-copper (I) complex can be efficiently synthesized.

<Mixing Step>

By mixing the rubeanic acid compound and the copper (I) compound as source compounds in the presence of a base, it is possible to obtain a black product of an electrically conductive substance which comprises the rubeanic acid-copper (I) complex.

Mixing does not particularly require heating or cooling and can be performed at room temperature.

Mixing time is not limited to a particular value and only needs to be adjusted as appropriate within a range of about 0.5 hours to about 48 hours depending on the amounts of the source compounds and other conditions.

Longer mixing time promotes the decomposition reaction of the rubeanic acid compound. Thus, from the perspective of producing copper (I) sulfide and/or copper (II) sulfide as by-products, it is preferred to lengthen the mixing time. On the other hand, from the perspective of increasing the yield of rubeanic acid-copper (I) complex, it is preferred to shorten the mixing time.

Mixing may be wet mixing performed in solution using a solvent or may be dry mixing performed without using a solvent.

In wet mixing, the base, rubeanic acid compound and copper (I) compound are added into a solvent to obtain a mixed solution, which can be mixed by known wet mixing methods. Specifically, examples of wet mixing include mixing using a mixer; stirring using a stirrer, a stirring bar, a stirring blade or the like; and dispersing using a wet pulverizer.

In the case of wet mixing, examples of solvents used include water such as purified water, pure water, and ion-exchanged water; organic solvents such as ethanol, methanol, and hexane; and mixtures thereof.

The amount of solvent used is not limited to a particular value and the solvent can be used in a volume of about 1 time to about 1000 times the volume of the source compounds.

The pH of the mixed solution only needs to be adjusted as appropriate from weak basicity to strong basicity of 8.0 to 14.0.

By performing wet mixing as described above, a black precipitate containing the rubeanic acid-copper (I) complex is formed in the mixed solution.

Dry mixing can be performed by charging the base, rubeanic acid compound and copper (I) compound into a reaction vessel and mixing them by dry mixing methods known in the art. Specifically, examples of dry mixing include mixing using a mixer, a mill, a kneader or the like with or without media. Inclusion of trace amounts of a liquid component during mixing facilitates the reaction. The liquid component can be selected from, for example, water and organic solvent.

In the case of dry mixing, a black product containing the rubeanic acid-copper (I) complex is obtained. This black product may contain moisture derived from the source compounds as a by-product.

<Filtrating Step>

When the rubeanic acid compound and copper (I) compound have been wet-mixed, the mixed solution containing the produced black precipitate is filtrated to remove the solvent, so that the black precipitate is isolated.

The method of filtrating the mixed solution is not limited to a particular one and filtration methods known in the art can be employed. Specifically, natural filtration, vacuum filtration, pressure filtration, centrifugal filtration, and other filtration methods can be used.

<Washing Step>

The black precipitate isolated by filtration after wet mixing or the black product obtained by dry mixing may be washed with an appropriate solvent to remove remaining impurities and by-products.

Solvents that can be used for washing only need to be selected as appropriate depending on the reaction solvent used and by-products that possibly remain. Examples of solvents include water, acetone, methanol, ethanol, hexane, toluene, and mixtures thereof.

<Drying Step>

The black precipitate or black product obtained through the optional washing step is dried to remove possible residual moisture and/or organic solvent, thereby affording an electrically conductive substance containing the rubeanic acid-copper (I) complex as a black powder.

The drying method is not limited to a particular one and drying methods known in the art can be employed. Specifically, examples of drying methods include drying under an inert gas atmosphere, high-temperature vacuum drying, freeze drying, natural drying, hot air drying, and spray drying.

EXAMPLES

The present disclosure will be detailed in more detail below with reference to Examples, which however shall not be construed as limiting the scope of the present disclosure.

[Evaluation of Chemical Composition]

The black powder obtained in each Example or Comparative Example as a test sample was analyzed by the methods described below to evaluate the chemical composition of the substance.

<Powder X-Ray Diffraction>

Powder X-ray diffraction was performed using a powder X-ray diffractometer ("RINT2000" manufactured by Rigaku Corporation) and the diffraction peaks of the obtained diffraction chart were compared with those of known compounds to identify the compounds contained in the test sample and estimate the chemical composition.

When a diffraction pattern clearly different from those of known compounds is observed, it can be estimated that the novel rubeanic acid-copper (I) complex is present. In addition, diffraction peaks having a full width at half maximum (FWHM) of 3° or less, characteristic of the novel rubeanic acid-copper (I) complex, are detected at diffraction angles (2θ) of around 22° and around 28°.

Note that diffraction peaks derived from the source compounds are observed at diffraction angles (2θ) of 16°, 31°, and 33°.

<IR Analysis>

Using a Fourier transform infrared spectrophotometer ("FT/IR-4100" manufactured by JASCO Corporation), infrared spectroscopic analysis was performed by the transmission method. The obtained IR analysis chart was analyzed to identify the compounds contained in the test sample and estimate the chemical composition.

When an IR spectrum clearly different from those of known compounds is observed, the presence of the novel rubeanic acid-copper (I) complex can be confirmed. When three characteristic infrared absorption peaks, derived from the source rubeanic acid's $NH_2$ group, are not observed at a wavenumber of around 3200 $cm^{-1}$ on the obtained IR analysis chart, it was determined that the presence of the novel rubeanic acid-copper (I) complex was confirmed.

<Confirmation of Coordination Bond to Copper Ion>

Coordinating atoms were determined from a comparison of data obtained by extended X-ray absorption fine structure (EXAFS) analysis of the test sample and simulation results obtained when assuming that the closest atom is sulfur or nitrogen. As a result, the presence of coordination bonds having a sulfur atom or a nitrogen atom as the coordinating atom was confirmed in all Examples and Comparative Examples.

<Confirmation of Rubeanic Acid Ligand>

Mass spectrometry was performed by detecting negative ions using a time-of-flight secondary ion mass spectrometer ("PHI TRIFT V nanoTOF" manufactured by ULVAC-PHI Incorporated). From the obtained mass spectrum, a fragment peak at mass number 118 assigned to rubeanic acid ligand was confirmed.

<Copper Ion Content Relative to Rubeanic Acid Ligand Content>

After confirming the presence of the rubeanic acid ligand by mass spectrometry as described above, thermogravimetric-differential thermal analysis (TG-DTA) was performed under a nitrogen stream, where weight loss on heating was measured by heating the test sample to 600° C. at a temperature elevation rate of 10° C./min. With the ash taken as copper (I) sulfide, the molar ratio of copper (I) ion content to rubeanic acid content was calculated.

<Proportion of Copper (I) Ions in Copper Ions>

X-ray absorption spectrum measurement was performed using BL14B2 beam line of synchrotron radiation facility SPring-8. X-ray absorption near edge structure (XANES) analysis was performed on the measurement result to find the proportion of copper (I) ions in the copper ions contained in the test sample.

[Evaluations of Physical Properties]

Using the evaluation methods described above, the black powder obtained in each Example or Comparative Example as a measurement sample was evaluated for electrical conductivity, porosity, crystallinity, and initial discharge characteristics.

<Electrical Conductivity>

3,000 mg of the measurement sample was weighed and electrical conductivity was measured by the four-probe method using an electric resistance meter ("Powder Resistance Measurement System" manufactured by MC Evolve Technologies Corporation). The results are shown in Table 1.

A higher electrical conductivity value indicates better electrical conductivity.

<Porosity>

100 mg of the measurement sample was weighed and nitrogen adsorption/desorption measurement by the BET method was performed using an automatic specific surface area analyzer ("BELSORP-mini II" manufactured by Bell Japan) with the pretreatment temperature being 140° C. The results are shown in Table 1.

A higher BET specific surface area value indicates higher porosity.

<Crystallinity>

The measurement sample was evaluated as having crystallinity when the diffraction chart of powder X-ray diffraction (hereinafter also referred to as "XRD chart") performed for substance identification had at least one diffraction peak not derived from the source compounds and having a full width at half maximum (FWHM) of 3° or less.

<Heat Resistance>

5 mg of the measurement sample was weighed and thermogravimetric measurement was performed by heating under nitrogen using a thermogravimetric analyzer ("TG/DTA 7200" manufactured by Seiko Instruments Inc.) to measure a 5% weight loss temperature. The results are shown in Table 1.

A higher 5% weight loss temperature indicates better heat resistance.

<Initial Discharge Characteristics>

A lithium ion battery was manufactured using the black powder obtained in each Example or Comparative Example as a positive electrode active material, and a charge/discharge test was performed to evaluate initial discharge characteristics.

40 parts by mass of the black powder obtained in each Example or Comparative Example, 40 parts by mass of acetylene black as a conductive aid, and 20 parts by mass of polytetrafluoroethylene (PTFE) as a binder were weighed and kneaded well. This kneaded product was pressed onto an aluminum foil having a thickness of 20 µm to form an electrode having a thickness of 60 µm for use as a positive electrode.

1M $LiPF_6$ was dissolved in a 1:1 (by mass) mixed solvent of ethylene carbonate and diethyl carbonate. The $LiPF_6$ solution was used as an electrolyte solution.

A microporous polyethylene having a thickness of 25 µm was used as a separator.

A Li metal foil having a thickness of 200 µm was bonded to a copper foil having a thickness of 20 µm to form a counter electrode (negative electrode).

A lithium ion battery was composed using these components and sealed in a coin battery type container to manufacture a test battery for evaluation.

The initial discharge capacity of the battery was measured by passing a current of 20 mA/g based on the weight of the black powder in the potential range of 4.4 to 0.5 V (vs $Li/Li^+$) at room temperature. The results are shown in Table 1.

(Synthesis Method and Evaluation Results)

As described below, organometallic substances were synthesized in Examples 1 to 5 and Comparative Examples 1 and 2 and the chemical compositions and physical properties of the obtained substances were evaluated. The results are also shown in Table 1.

Example 1

In an argon glove box (closed system, under an argon atmosphere), 1 mmol (120 mg) of rubeanic acid and 2 mmol (82 mg) of $LiOH.H_2O$ were placed in a flask, 20 mL of ion-exchanged water was added, and the mixture was stirred at room temperature for 1 hour. Next, 2 mmol (198 mg) of copper (I) chloride was added and stirred at room temperature for 24 hours. The produced black precipitate was filtrated, washed with water and acetone, and dried under vacuum at 80° C. to afford a black powder.

The obtained black powder showed a powder X-ray diffraction pattern not identical to those of existing compounds (FIG. 1). The IR spectrum was also different from those of the source compounds (FIG. 2). A fragment peak at mass number 118 assigned to rubeanic acid ligand was also confirmed. The molar ratio of rubeanic acid ligands to copper ions in the complex was 1:2. The proportion of Cu (I) ions in the Cu ions in the complex was estimated to be 100 mol %.

The obtained black powder showed a relatively high electrical conductivity of $2.0 \times 10^{-4}$ S/cm and hence was confirmed to be an electrically conductive substance. The black powder had a BET specific surface area of 156 m²/g and hence was confirmed to be a porous substance.

In the XRD chart (FIG. 1), a diffraction peak having a full width at half maximum (FWHM) of not greater than 1° was observed near the diffraction angle (2θ) of 28°, confirming that the black powder was a crystalline substance. The black powder had a 5% weight loss temperature of 215° C. and hence was confirmed to have heat resistance. As a result of the charge/discharge test, the initial discharge capacity was 406 mAh/g and hence it was confirmed that the lithium ion battery had excellent initial discharge characteristics.

Example 2

With the experimental system being opened to the atmosphere, 1 mmol (120 mg) of rubeanic acid and 2 mmol (82 mg) of LiOH.H₂O were put into a flask, 20 mL of ion-exchanged water was added, and the mixture was stirred at room temperature for 1 hour. Next, 1.3 mmol (119 mg) of copper (I) chloride was added and the mixture was stirred at room temperature for 24 hours. The produced black precipitate was filtered, washed with water and acetone, and dried under vacuum at 80° C. to afford a black powder.

Figure 3:
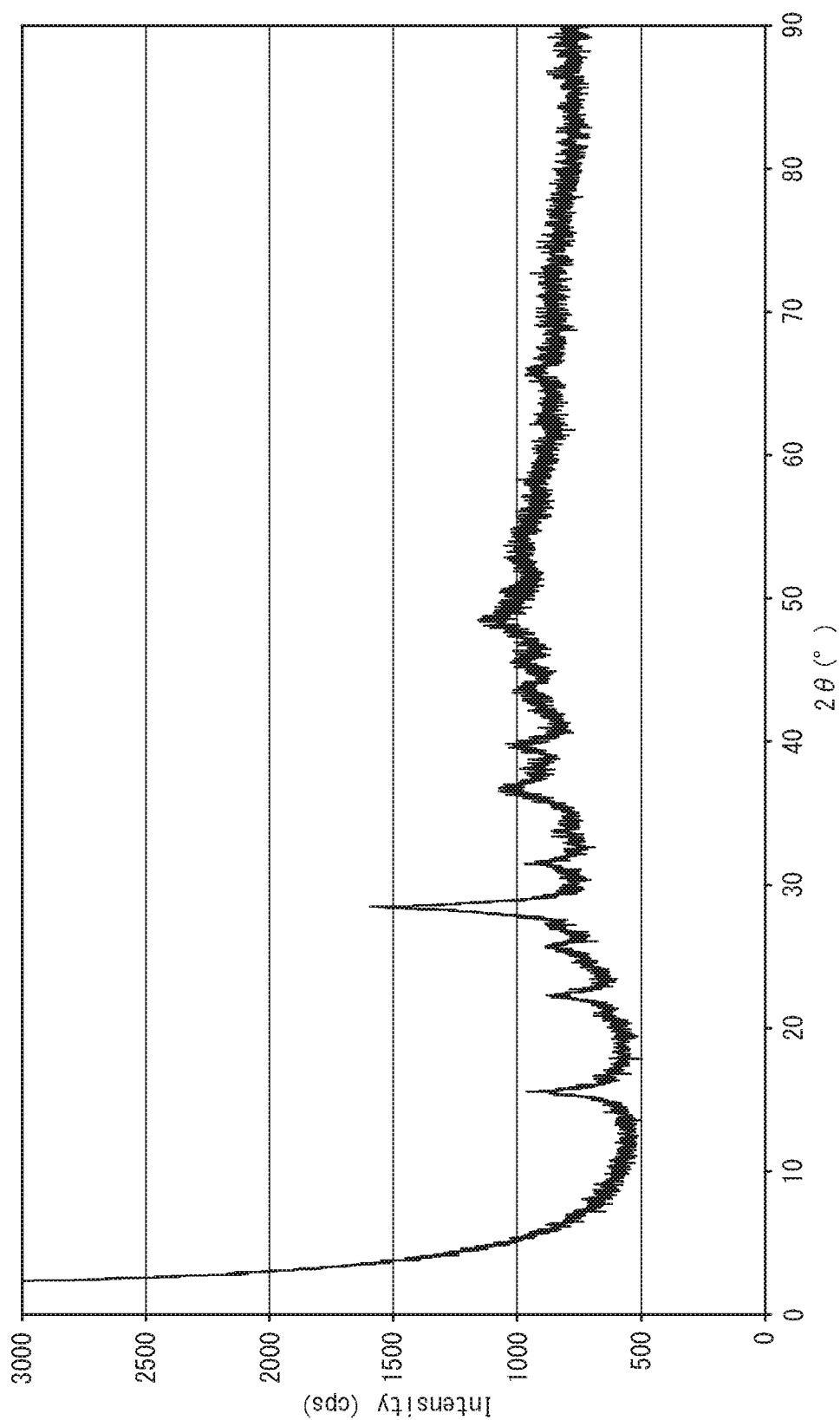
FIG. 3 is a powder X-ray diffraction chart of an electrically conductive substance obtained in Example 2.

The obtained black powder showed a powder X-ray diffraction pattern not identical to those of existing compounds (FIG. 3). The IR spectrum was also different from those of the source compounds (FIG. 4). A fragment peak at mass number 118 assigned to rubeanic acid ligand was also confirmed. The molar ratio of rubeanic acid ligands to copper ions in the complex was 1:1.3. The proportion of Cu (I) ions in the Cu ions in the complex was estimated to be 46 mol %. The reason for this appears to be because synthesis performed in an open system caused some of the Cu (I) ions to be oxidized to Cu (II) ions.

The obtained black powder showed a high electrical conductivity of 2.0 S/cm and hence was confirmed to be an excellent electrically conductive substance. The black powder had a BET specific surface area of 138 m²/g and hence was confirmed to be a porous substance. In the XRD chart (FIG. 3), a diffraction peak having a full width at half maximum (FWHM) of not greater than 1° was observed near the diffraction angle (2θ) of 28°, confirming that the black powder was a crystalline substance. The black powder had a 5% weight loss temperature of 214° C. and hence was confirmed to have heat resistance. As a result of the charge/discharge test, the initial discharge capacity was 418 mAh/g and hence it was confirmed that the lithium ion battery had excellent initial discharge characteristics.

Example 3

Stirring was carried out as in Example 2 except that 4 mmol (164 mg) of LiOH.H₂O was used with the experimental system being opened to the atmosphere. The produced black precipitate was filtered, washed with water and acetone, and dried under vacuum at 80° C. to afford a black powder.

Figure 5:
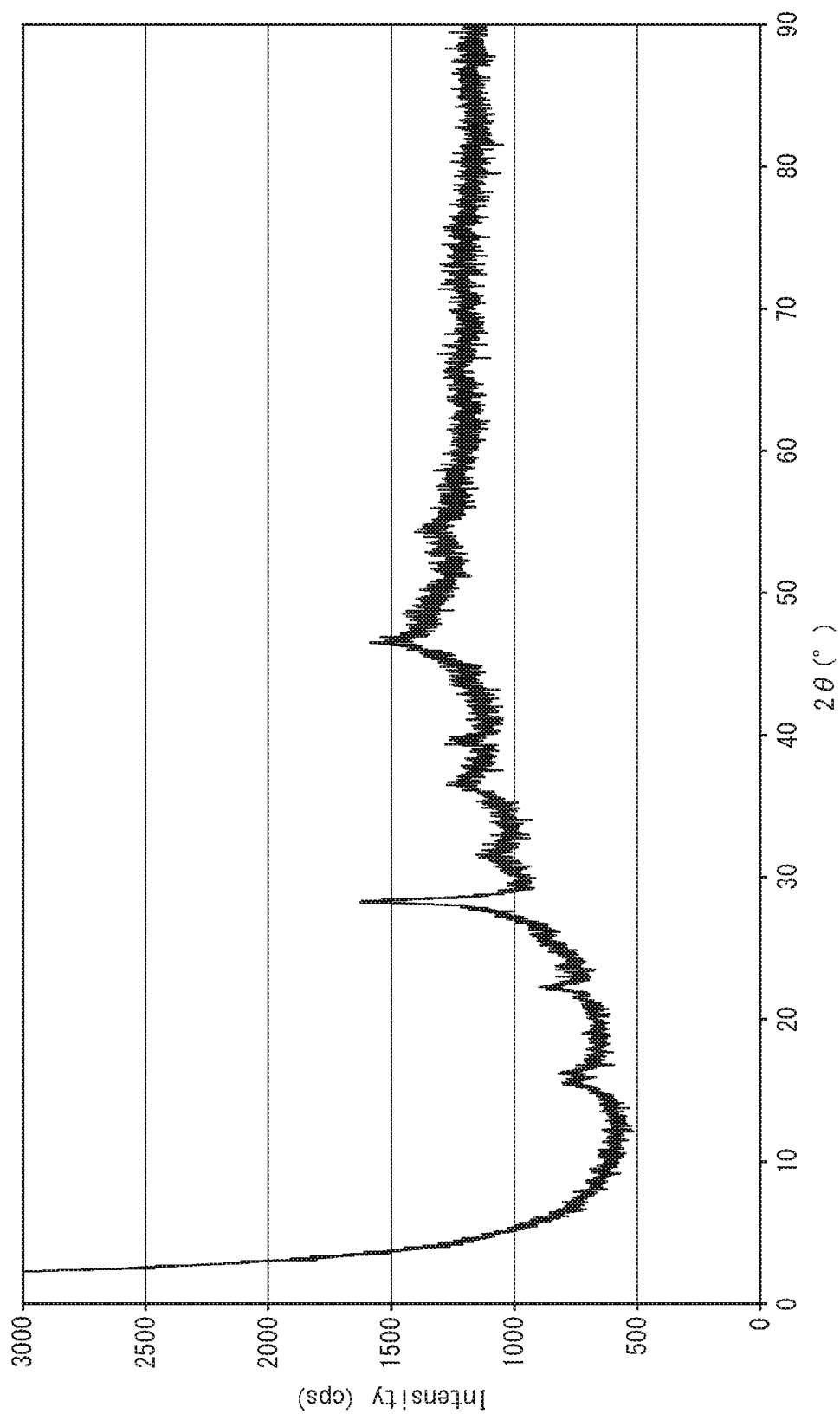
FIG. 5 is a powder X-ray diffraction chart of an electrically conductive substance obtained in Example 3.
Figure 6:
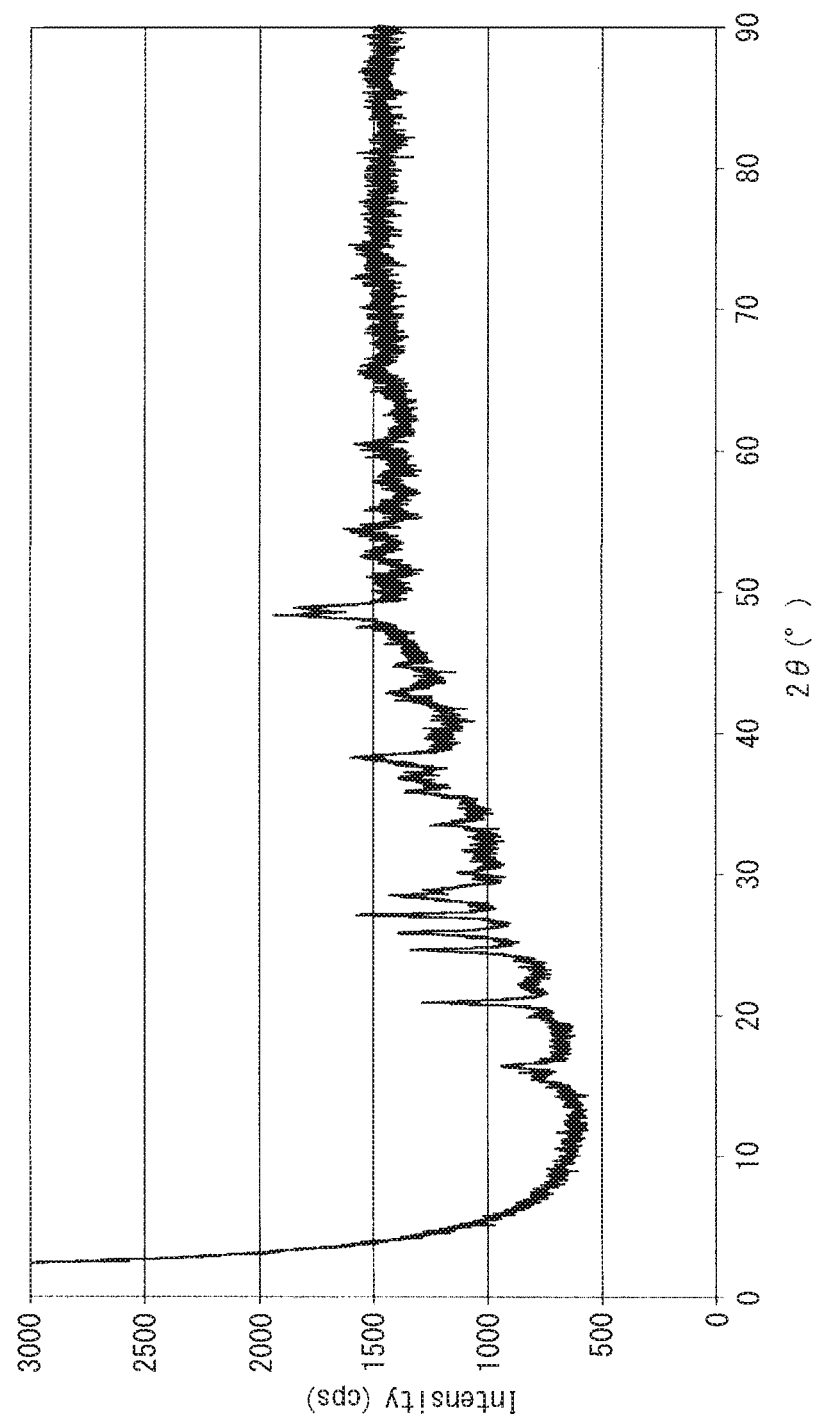
FIG. 6 is a powder X-ray diffraction chart of an electrically conductive substance obtained in Example 4.

The obtained black powder showed a powder X-ray diffraction pattern not identical to those of existing compounds (FIG. 5). The IR spectrum was also different from those of the source compounds. Mass spectrometry of the product confirmed a fragment at mass number 118 assigned to rubeanic acid. The molar ratio of rubeanic acid ligands to copper ions in the complex was 1:4.2. Because this molar ratio is higher than the stoichiometric equivalent ratio that can be deduced from the positive charge of the metal and the negative charge of the ligand, it is presumed that the copper ions form clusters in the complex. The proportion of Cu (I) ions in the Cu ions in the complex was estimated to be 70 mol %.

The obtained black powder showed an extremely high electrical conductivity of $4.0 \times 10^2$ S/cm and hence was confirmed to be an extremely excellent electrically conductive substance. In the XRD chart (FIG. 5), a diffraction peak having a full width at half maximum (FWHM) of not greater than 1° was observed near the diffraction angle (2θ) of 28°, confirming that the black powder was a crystalline substance. The black powder had a BET specific surface area of 164 m²/g and hence was confirmed to be a porous substance. The black powder had a 5% weight loss temperature of 217° C. and hence was confirmed to have heat resistance. As a result of the charge/discharge test, the initial discharge capacity was 385 mAh/g and hence it was confirmed that the lithium ion battery had excellent initial discharge characteristics.

Example 4

A synthesis reaction was performed as in Example 1 except that as a base NaOH was used instead of LiOH.H₂O to afford a black powder.

The obtained black powder showed a powder X-ray diffraction pattern (FIG. 6) and an IR spectrum (FIG. 7) similar to those of the black powder obtained in Example 1. Thus, it was able to determine that an electrically conductive substance similar to that obtained in Example 1 was successfully obtained. The obtained black powder had a BET specific surface area of 156 m²/g and hence was confirmed to be a porous substance.

Example 5

In an argon glove box (closed system, under argon atmosphere), 1 mmol (120 mg) of rubeanic acid, 2 mmol (82 mg) of LiOH.H₂O and 2 mmol (198 mg) of copper (I) chloride were placed in a ball mill container such that the composition of the source material becomes the same as that in Example 1, and 2 mm glass beads were loaded to about 80% of the container and the ball mill was rotated at room temperature for 2 hours. The produced black product was filtered off, washed with water and acetone, and dried under vacuum at 80° C. to afford a black powder.

The obtained black powder showed a powder X-ray diffraction pattern and an IR spectrum similar to those of the black powder obtained in Example 1. Thus, it was able to determine that an electrically conductive substance similar to that obtained in Example 1 was successfully obtained as in Example 4. The obtained black powder had a BET specific surface area of 156 m²/g and hence was confirmed to be a porous substance.

Comparative Example 1

Figure 8:
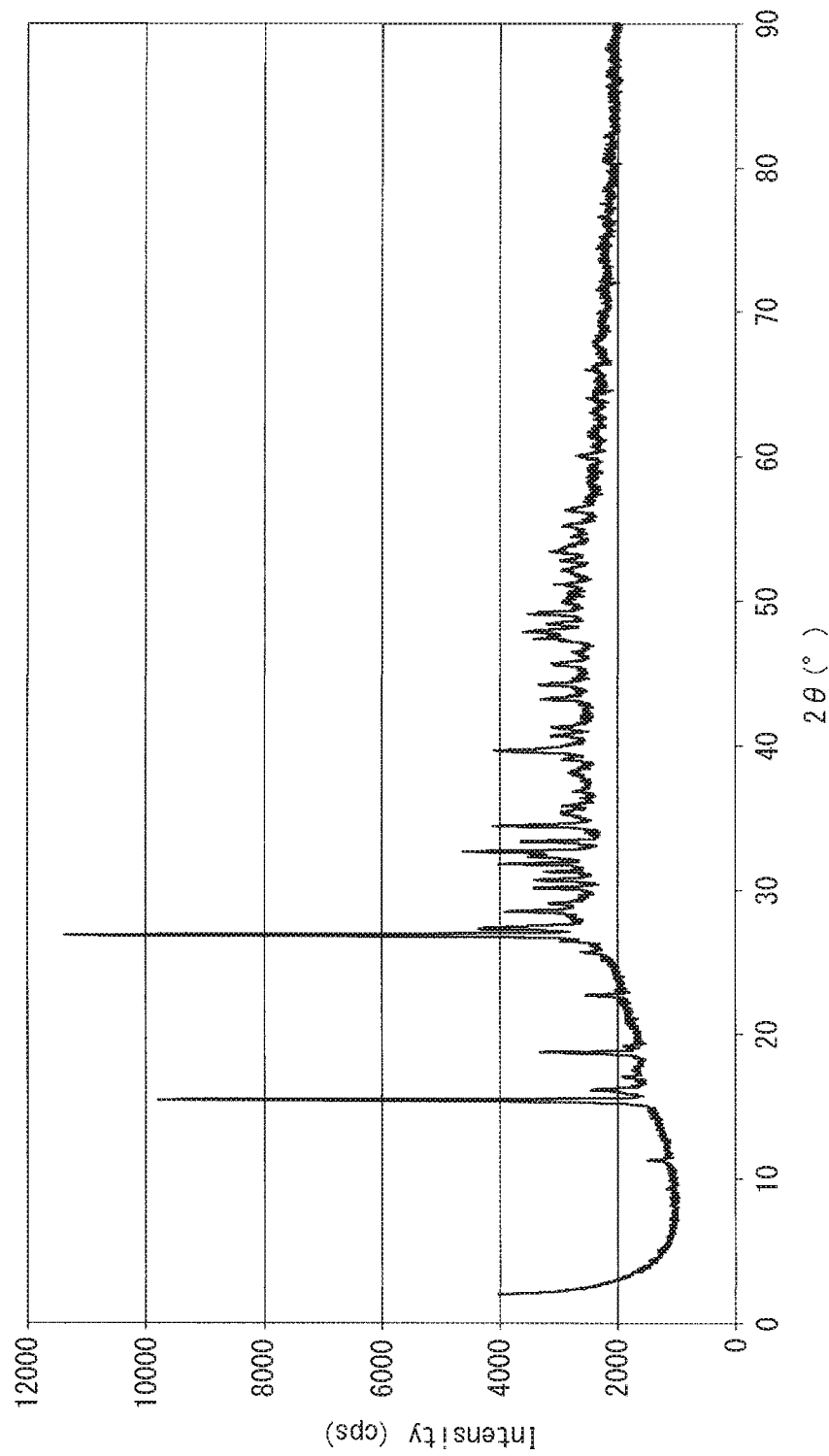
FIG. 8 is a powder X-ray diffraction chart of a substance (rubeanic acid-copper (I) chloride complex) obtained in Comparative Example 1.

In an argon glove box (closed system, under argon atmosphere), 1 mmol (120 mg) of rubeanic acid and 1 mmol (99 mg) of copper (I) chloride were placed in a flask, and 20 mL of ethanol was added and stirred for 24 hours. The produced black precipitate was filtered, washed with water and acetone, and dried under vacuum at 80° C. By powder X-ray diffraction, the obtained compound was identified to be a rubeanic acid-Cu (I) Cl complex ($C_2H_4S_2N_2Cu(I)Cl$), a 1:1 complex of rubeanic acid and copper (I) chloride. The proportion of Cu (I) ions in the Cu ions in the complex was estimated to be 100 mol %. By the nitrogen adsorption/ desorption measurement, the obtained compound had a BET specific surface area of 2 m²/g and hence was found not to be a porous substance. From the XRD chart (FIG. 8), the obtained powder was found to be a crystalline substance. For the obtained powder, an attempt was made to measure electric conductivity as in Example 1, but measurement failed because the powder was electrically insulating. The 5% weight loss temperature on heating under nitrogen using a thermogravimetric analyzer was 187° C. When this powder was evaluated as a lithium ion battery electrode, an initial discharge capacity of 130 mAh/g was obtained.

Comparative Example 2

In an argon glove box (closed system, under argon atmosphere), 1 mmol (120 mg) of rubeanic acid and 1 mmol (255 mg) of copper (II) sulfate pentahydrate were put in separate flasks, 20 mL of ethanol and 20 mL of ion exchange water were added in the respective flasks, and then both were combined and stirred for 24 hours.

The produced black precipitate was filtrated, washed with water and acetone, and dried under vacuum at 80° C. By powder X-ray diffraction and IR, the obtained compound was identified to be a rubeanic acid-Cu (II) complex ($C_2H_2S_2N_2Cu(II)$), a 1:1 complex of rubeanic acid and copper (II). By the nitrogen adsorption/desorption measurement, the obtained compound had a BET specific surface area of 52 m²/g and hence was found to be a porous substance. From the XRD chart (FIG. 10), the obtained powder was found not to be a crystalline substance. The electrical conductivity of the obtained powder measured as in Example 1 was found to be $4.0 \times 10^{-6}$ S/cm. The 5% weight loss temperature on heating under nitrogen was 195° C. When this powder was evaluated as a lithium ion battery electrode, an initial discharge capacity of 200 mAh/g was obtained.

The results of Examples and Comparative Examples are shown in Table 1 below.

TABLE 1

| | | | | Ex 1 | Ex 2 | Ex 3 |
|---|---|---|---|---|---|---|
| Production condition | Rubeanic acid compound | Type | [—] | $C_2H_4S_2N_2$ | $C_2H_4S_2N_2$ | $C_2H_4S_2N_2$ |
| | | Amount used | [mmol] | 1 | 1 | 1 |
| | Copper compound | Type | [—] | CuCl | CuCl | CuCl |
| | | Amount used | [mmol] | 2 | 1.3 | 1.3 |
| | Base | Type | [—] | LiOH•$H_2O$ | LiOH•$H_2O$ | LiOH•$H_2O$ |
| | | Amount used | [mmol] | 2 | 2 | 4 |
| | Rubeanic acid compound:base | | [molar ratio] | 1:2 | 1:2 | 1:4 |
| | Experiment system | | [—] | Closed | Open | Open |
| | Mixing method | | [—] | Wet | Wet | Wet |
| Chemical conposition | Peak at mass number of 118 | | [—] | Observed | Observed | Observed |
| | Ligand:copper (I + II) ions | | [molar ratio] | 1:2 | 1:1.3 | 1:4.2 |
| | Proportion of copper (I) ions in copper ions | | [mol %] | 100 | 46 | 70 |
| Physical properties | BET specific surface area | | [m²/g] | 156 | 138 | 164 |
| | Peak having FWHM of 3° or less | | [—] | Observed | Observed | Observed |
| | Electrical conductivity | | [S/cm] | $2.0 \times 10^{-4}$ | 2.0 | $4.0 \times 10^2$ |
| | 5% weight loss temperature | | [° C.] | 215 | 214 | 217 |
| | Initial discharge capacity | | [mAh/g] | 406 | 418 | 385 |

| | | | Ex 4 | Ex 5 | Comp. Ex 1 | Comp. Ex 2 |
|---|---|---|---|---|---|---|
| Production condition | Rubeanic acid compound | Type | $C_2H_4S_2N_2$ | $C_2H_4S_2N_2$ | $C_2H_4S_2N_2$ | $C_2H_4S_2N_2$ |
| | | Amount used | 1 | 1 | 1 | 1 |
| | Copper compound | Type | CuCl | CuCl | CuCl | $CuSO_4 \cdot 5H_2O$ |
| | | Amount used | 2 | 2 | 1 | 1 |
| | Base | Type | NaOH | LiOH•$H_2O$ | — | — |
| | | Amount used | 2 | 2 | — | — |
| | Rubeanic acid compound:base | | 1:2 | 1:2 | — | — |
| | Experiment system | | Closed | Closed | Closed | Closed |
| | Mixing method | | Wet | Dry | Wet | Wet |
| Chemical conposition | Peak at mass number of 118 | | Observed | Observed | Observed | Observed |
| | Ligand:copper (I + II) ions | | 1:2 | 1:2 | 1:1 | 1:1 |
| | Proportion of copper (I) ions in copper ions | | 100 | 100 | 100 | 0 |
| Physical properties | BET specific surface area | | 156 | 156 | 2 | 52 |
| | Peak having FWHM of 3° or less | | Observed | Observed | Observed | Not observed |
| | Electrical conductivity | | — | — | Insulating | $4.0 \times 10^{-6}$ |
| | 5% weight loss temperature | | — | — | 187 | 195 |
| | Initial discharge capacity | | — | — | 130 | 200 |

From comparisons of the results of Examples and Comparative Examples shown in Table 1, the compounds of Examples 1 to 5, which are electrically conductive substances comprising a complex containing rubeanic acid ligands and copper (I) ions, showed significantly improved electrical conductivity, porosity, and heat resistance compared to the compound of Comparative Example 1, which is an electrically conductive substance comprising the rubeanic acid-copper (I) chloride complex, and the compound of Comparative Example 2, which is an electrically conductive substance consisting only of the rubeanic acid-copper (II) complex. The lithium ion batteries including a positive electrode formed using the disclosed electrically conductive substance have high initial discharge characteristics.

Because crystallinity and high large specific surface area were observed, it is estimated that the rubeanic acid-copper (I) complex contained in each of the compounds obtained in Examples 1 to 5 is a coordination polymer complex analogous to an MOF.

INDUSTRIAL APPLICABILITY

The disclosed electrically conductive substance can be suitably used as an active material of power storage devices (e.g., LIBs, SIBs, MgIBs, AlIBs, EDLCs, and LICs) and as an electrode catalyst of fuel cells.

The disclosed electrically conductive substance can be suitably used also as a catalyst and a porous material as a gas adsorbent or separator.

The invention claimed is:

1. An electrically conductive substance comprising a complex containing rubeanic acid ligands and copper ions, wherein the copper ions comprise copper (I) ions, and a molar ratio of copper ion content to rubeanic acid ligand content is 1.2 or more.

2. The electrically conductive substance of claim 1, wherein a proportion of the copper (I) ions in the copper ions is 20 mol % or more.

3. The electrically conductive substance of claim 1, wherein the electrically conductive substance has crystallinity.

4. The electrically conductive substance of claim 1, wherein the electrically conductive substance has a BET specific surface area of 20 m2/g or more.

5. The electrically conductive substance of claim 1, wherein a molar ratio of copper ion content to rubeanic acid ligand content is 2.0 or more.

6. The electrically conductive substance of claim 1, further comprising copper (I) sulfide and/or copper (II) sulfide.

7. An electrode for a power storage device, comprising the electrically conductive substance of claim 1.

8. An electrode for a fuel cell, comprising the electrically conductive substance of claim 1.

9. A catalyst comprising the electrically conductive substance of claim 1.

10. A porous material comprising the electrically conductive substance of claim 1.

11. A method of producing an electrically conductive substance which comprises a complex containing rubeanic acid ligands and copper ions, at a molar ratio of copper ion content to rubeanic acid ligand content is 1.2 or more, the method comprising:
mixing a rubeanic acid compound and a copper (I) compound in the presence of a base to provide an electrically conductive substance which comprises a complex containing rubeanic acid ligands and copper ions,
wherein the copper ions comprise copper (I) ions.

12. The method of producing an electrically conductive substance of claim 11, wherein the rubeanic acid compound and the base are used in a molar ratio of 1:0.3 to 1:5.

13. The method of producing an electrically conductive substance of claim 11, wherein the base is at least one selected from the group consisting of alkali metal hydroxides, trialkylamines, and pyridines.

14. The method of producing an electrically conductive substance of claim 11, wherein the copper (I) compound is at least one selected from the group consisting of copper (I) chloride, copper (I) bromide, copper (I) iodide, copper (I) thiocyanate, copper (I) acetate, copper (I) sulfide, and copper (I) oxide.

* * * * *